US008075885B2

(12) United States Patent
Bebbington et al.

(10) Patent No.: US 8,075,885 B2
(45) Date of Patent: Dec. 13, 2011

(54) METHODS OF TREATING HEART FAILURE USING AN ANTI-GM-CSF ANTIBODY

(75) Inventors: Christopher R. Bebbington, San Mateo, CA (US); Geoffrey T. Yarranton, Burlingame, CA (US)

(73) Assignee: KaloBios Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 12/419,991

(22) Filed: Apr. 7, 2009

(65) Prior Publication Data

US 2009/0263387 A1     Oct. 22, 2009

Related U.S. Application Data

(60) Provisional application No. 61/043,026, filed on Apr. 7, 2008.

(51) Int. Cl.
*A61K 39/00* (2006.01)
(52) U.S. Cl. ............... 424/130.1; 424/133.1; 424/135.1; 424/141.1; 424/142.1
(58) Field of Classification Search .................. None
See application file for complete search history.

(56) References Cited

U.S. PATENT DOCUMENTS

| 2004/0053365 A1 | 3/2004 | Renner et al. |
| 2005/0233992 A1 | 10/2005 | Itescu |

FOREIGN PATENT DOCUMENTS

| EP | 0499161 A1 | 8/1992 |
| EP | 0499162 A1 | 8/1992 |
| WO | WO 2007/092939 A1 | 8/2007 |
| WO | WO 2007/110631 A1 | 10/2007 |
| WO | WO 2008/052277 A1 | 5/2008 |

OTHER PUBLICATIONS

Bowie et al., 1990, Science 247: 1306-1310.*
Wells, 1990, Biochemistry 29:8509-8517.*
Adamopoulos, S. et al.; "Physical training reduces peripheral markers of inflammation in patients with chronic heart failure"; 2001. *European Heart Journal*, vol. 22, pp. 791-797.
Kawai, Chuichi; "From Myocarditis to Cardiomyopathy: Mechanisms of Inflammation and Cell Death: Learning From the Past for the Future"; 1999, *Circulation*, vol. 99, pp. 1091-1100.
Kishimoto, Chiharu et al.; "Treatment of acute inflammatory cardiomyopathy with intravenous immunoglobulin ameliorates left ventricular function associated with suppression of inflammatory cytokines and decreased oxidative stress"; 2003, *International Journal of Cardiology*, vol. 91, pp. 173-178.
Lancaster, Jordan J. et al.; "Granulocyte—macrophage colony—stimulating factor antibody improves left ventricular function and limits maladaptive remodeling following myocardial infarction"; 2008, *Journal of Cardiac Failure*, vol. 14, No. 6, abstract 132, p. S42.
Maekawa, Yuichiro et al.; "Effect of Granulocyte-Macrophage Colony-Stimulating Factor Inducer on Left Ventricular Remodeling After Acute Myocardial Infarction"; 2004, *Journal of the American College of Cardiology*, vol. 44, No. 7, pp. 1510-1520.
Postiglione, L. et al.; "Granulocyte Macrophage-Colony Stimulating Factor receptor expression on human cardiomyocytes from end-stage heart failure patients"; 2006, *European Journal of Heart Failure*, vol. 8, No. 6, pp. 564-570.
Seiler, Christian et al.; "Promotion of Collateral Growth by Granulocyte-Macrophage Colony-Stimulating Factor in Patients with Coronary Artery Disease: A Randomized, Double-Blind, Placebo-Controlled Study"; 2001, *Circulation*, vol. 104, pp. 2012-2017.
Rutschow, Susanne et al.; "Myocardial proteases and matrix remodeling in inflammatory heart disease"; 2006, *Cardiovascular Research*, vol. 69, pp. 646-656.

* cited by examiner

*Primary Examiner* — Gyan Chandra
(74) *Attorney, Agent, or Firm* — Kilpatrick Townsend & Stockton LLP

(57) ABSTRACT

This invention relates to methods of treating a patient suffering from heart failure, or a patient at risk for heart failure, using a GM-CSF antagonist.

28 Claims, 9 Drawing Sheets

FIGURE 9

```
VH1 1-02  QVQLVQSGAEVKKPGASVKVSCKASGYTFTGYYMHWVRQAPGQGLEWMGWINPNSGGTNYAQKFQGRVTMTRDTSISTAYMELSRLRSDDTAVYYCAR------------------------------------
VH#1      QVQLVQSGAEVKKPGASVKVSCKASGYTFTGYYMHWVRQAPGQGLEWMGWINPNSGGTNYAQKFQGRVTMTRDTSISTAYMELSRLRSDDTAVYYCVRRDRFPYYFDYWGQGTLVTVSS

VH1 1-03  QVQLVQSGAEVKKPGASVKVSCKASGYTFTSYAMHWVRQAPGQRLEWMGWINAGNGNTKYSQKFQGRVTITRDTSASTAYMELSSLRSEDTAVYYCAR------------------------------------
VH#2      QVQLVQSGAEVKKPGASVKVSCKASGYSFTNYYIHWVRQAPGQRLEWMGWINAGNGNTKYSQKFQGRVAITRDTSASTAYMELSSLRSEDTAVYYCARRDRFPYYFDYWGQGTLVTVSS
VH#3      QVQLVQSGAEVKKPGASVKVSCKASGYSFTNYYIHWVRQAPGQRLEWMGWINAGNGNTKYSQKFQGRVAITRDTSASTAYMELSSLRSEDTAVYYCARRQRFPYYFDYWGQGTLVTVSS
VH#4      QVQLVQSGAEVKKPGASVKVSCKASGYSFTNYYIHWVRQAPGQRLEWMGWINAGNGNTKYSQKFQGRVAITRDTSASTAYMELSSLRSEDTAVYYCVRRQRFPYYFDYWGQGTLVTVSS
VH#5      QVQLVQSGAEVKKPGASVKVSCKASGYSFTNYYIHWVRQAPGQRLEWMGWINAGNGNTKYSQKFQGRVTITRDTSASTAYMELSSLRSEDTAVYYCVRRQRFPYYFDYWGQGTLVTVSS

VKIII A27 EIVLTQSPGTLSLSPGERATLSCRASQSVSSSYLAWYQQKPGQAPRLLIYGASSRATGIPDRFSGSGSGTDFTLTISRLEPEDFAVYYCQQYGSSP-----
VK#1      EIVLTQSPATLSVSPGERATLSCRASQSVGTN-VAWYQQKPGQAPRVLIYSTSSRATGITDRFSGSGSGTDFTLTISRLEPEDFAVYYCQQFNKSPLIFGGGTKVEIK
VK#2      EIVLTQSPATLSVSPGERATLSCRASQSVGTN-VAWYQQKPGQAPRVLIYSTSSRATGITDRFSGSGSGTDFTLTISRLEPEDFAVYYCQQFNKSPLIFGGGTKVEIK
VK#3      EIVLTQSPATLSVSPGERATLSCRASQSIGSN-LAWYQQKPGQAPRVLIYSTSSRATGITDRFSGSGSGTDFTLTISRLEPEDFAVYYCQQFNKSPLIFGGGTKVEIK
VK#4      EIVLTQSPATLSVSPGERATLSCRASQSIGSN-LAWYQQKPGQAPRVLIYSTSSRATGITDRFSGSGSGTDFTLTISRLEPEDFAVYYCQQFNKSPLIFGGGTKVEIK
```

| Fab | Vh | Vk | Dissociation rate for binding to GM-CSF determined by surface plasmon resonance analysis ($s^{-1}$) |
|---|---|---|---|
| FB42-8 | #2 | #3 | $1.36 \times 10^{-4}$ |
| FB44-5 | #1 | #3 | $8.0 \times 10^{-5}$ |
| FB77-2 | #3 | #1 | $5.57 \times 10^{-5}$ |
| FB92-1 | #4 | #4 | $3.84 \times 10^{-5}$ |
| FB94-1 | #4 | #2 | $3.12 \times 10^{-5}$ |
| FB104-1 | #5 | #1 | $3.57 \times 10^{-5}$ |
| FB106-1 | #5 | #2 | $5.4 \times 10^{-5}$ |

SEQUENCE LISTING

<160> NUMBER OF SEQ ID NOS: 38

<210> SEQ ID NO 1
<211> LENGTH: 140
<212> TYPE: PRT
<213> ORGANISM: Artificial Sequence
<220> FEATURE:
<223> OTHER INFORMATION: synthetic murine anti-granulocyte macrophage
      colony stimulating factor (GM-CSF) antibody 19/2
      heavy chain variable region (V-H)

<400> SEQUENCE: 1

Met Glu Leu Ile Met Leu Phe Leu Leu Ser Gly Thr Ala Gly Val His
 1               5                  10                  15

Ser Glu Val Gln Leu Gln Gln Ser Gly Pro Glu Leu Val Lys Pro Gly
            20                  25                  30

Ala Ser Val Lys Ile Ser Cys Lys Ala Ser Gly Tyr Thr Phe Thr Asp
        35                  40                  45

Tyr Asn Ile His Trp Val Lys Gln Ser His Gly Lys Ser Leu Asp Trp
    50                  55                  60

Ile Gly Tyr Ile Ala Pro Tyr Ser Gly Gly Thr Gly Tyr Asn Gln Glu
65                  70                  75                  80

Phe Lys Asn Arg Ala Thr Leu Thr Val Asp Lys Ser Ser Ser Thr Ala
                85                  90                  95

Tyr Met Glu Leu Arg Ser Leu Thr Ser Asp Asp Ser Ala Val Tyr Tyr
            100                 105                 110

Cys Ala Arg Arg Asp Arg Phe Pro Tyr Tyr Phe Asp Tyr Trp Gly Gln
        115                 120                 125

Gly Thr Thr Leu Arg Val Ser Ser Val Ser Gly Ser
    130                 135                 140

<210> SEQ ID NO 2
<211> LENGTH: 150
<212> TYPE: PRT
<213> ORGANISM: Artificial Sequence

```
<220> FEATURE:
<223> OTHER INFORMATION: synthetic murine anti-granulocyte macrophage
      colony stimulating factor (GM-CSF) antibody 19/2
      light chain variable region (V-L)

<400> SEQUENCE: 2

Met Gly Phe Lys Met Glu Ser Gln Ile Gln Val Phe Val Tyr Met Leu
 1               5                  10                  15

Leu Trp Leu Ser Gly Val Asp Gly Asp Ile Val Met Ile Gln Ser Gln
            20                  25                  30

Lys Phe Val Ser Thr Ser Val Gly Asp Arg Val Asn Ile Thr Cys Lys
                35                  40                  45

Ala Ser Gln Asn Val Gly Ser Asn Val Ala Trp Leu Gln Gln Lys Pro
        50                  55                  60

Gly Gln Ser Pro Lys Thr Leu Ile Tyr Ser Ala Ser Tyr Arg Ser Gly
65                  70                  75                  80

Arg Val Pro Asp Arg Phe Thr Gly Ser Gly Ser Gly Thr Asp Phe Ile
                85                  90                  95

Leu Thr Ile Thr Thr Val Gln Ser Glu Asp Leu Ala Glu Tyr Phe Cys
            100                 105                 110

Gln Gln Phe Asn Arg Ser Pro Leu Thr Phe Gly Ser Gly Thr Lys Leu
                115                 120                 125

Glu Leu Lys Arg Ala Asp Ala Ala Pro Thr Val Ser Ile Phe Pro Pro
            130                 135                 140

Ser Ser Lys Gly Glu Phe
145                 150

<210> SEQ ID NO 3
<211> LENGTH: 6
<212> TYPE: PRT
<213> ORGANISM: Artificial Sequence
<220> FEATURE:
<223> OTHER INFORMATION: synthetic anti-granulocyte macrophage colony
      stimulating factor (GM-CSF) antibody heavy chain
      variable region (V-H) complementarity-determining
      region 3 (CDR3) binding specificity determinant (BSD)

<400> SEQUENCE: 3

Arg Gln Arg Phe Pro Tyr
 1               5

<210> SEQ ID NO 4
<211> LENGTH: 6
<212> TYPE: PRT
<213> ORGANISM: Artificial Sequence
<220> FEATURE:
<223> OTHER INFORMATION: synthetic anti-granulocyte macrophage colony
      stimulating factor (GM-CSF) antibody heavy chain
      variable region (V-H) complementarity-determining
      region 3 (CDR3) binding specificity determinant (BSD)

<400> SEQUENCE: 4

Arg Asp Arg Phe Pro Tyr
 1               5

<210> SEQ ID NO 5
<211> LENGTH: 15
<212> TYPE: PRT
<213> ORGANISM: Artificial Sequence
<220> FEATURE:
<223> OTHER INFORMATION: synthetic anti-granulocyte macrophage colony
      stimulating factor (GM-CSF) antibody heavy chain
      variable region (V-H) human J-segment JH4

<400> SEQUENCE: 5

Tyr Phe Asp Tyr Trp Gly Gln Gly Thr Leu Val Thr Val Ser Ser
1               5                   10                  15

<210> SEQ ID NO 6
<211> LENGTH: 10
<212> TYPE: PRT
<213> ORGANISM: Artificial Sequence
<220> FEATURE:
<223> OTHER INFORMATION: synthetic anti-granulocyte macrophage colony
      stimulating factor (GM-CSF) antibody heavy chain
      variable region (V-H) complementarity-determining
      region 3 (CDR3)

<400> SEQUENCE: 6

Arg Gln Arg Phe Pro Tyr Tyr Phe Asp Tyr
1               5                   10

<210> SEQ ID NO 7
<211> LENGTH: 10
<212> TYPE: PRT
<213> ORGANISM: Artificial Sequence
<220> FEATURE:
<223> OTHER INFORMATION: synthetic anti-granulocyte macrophage colony
      stimulating factor (GM-CSF) antibody heavy chain
      variable region (V-H) complementarity-determining
      region 3 (CDR3, CDRH3)

<400> SEQUENCE: 7

Arg Asp Arg Phe Pro Tyr Tyr Phe Asp Tyr
1               5                   10

<210> SEQ ID NO 8
<211> LENGTH: 9
<212> TYPE: PRT
<213> ORGANISM: Artificial Sequence
<220> FEATURE:
<223> OTHER INFORMATION: synthetic anti-granulocyte macrophage colony
      stimulating factor (GM-CSF) antibody light chain
      variable region (V-L) complementarity-determining
      region 3 (CDR3)
<221> NAME/KEY: VARIANT
<222> LOCATION: (5)...(5)
<223> OTHER INFORMATION: Xaa = Lys or Arg

<400> SEQUENCE: 8

Gln Gln Phe Asn Xaa Ser Pro Leu Thr
1               5

<210> SEQ ID NO 9
<211> LENGTH: 9
<212> TYPE: PRT
<213> ORGANISM: Artificial Sequence
<220> FEATURE:
<223> OTHER INFORMATION: synthetic anti-granulocyte macrophage colony
      stimulating factor (GM-CSF) antibody light chain
      variable region (V-L) complementarity-determining
      region 3 (CDR3)

<400> SEQUENCE: 9

Gln Gln Phe Asn Lys Ser Pro Leu Thr
1               5

<210> SEQ ID NO 10
<211> LENGTH: 98
<212> TYPE: PRT
<213> ORGANISM: Homo sapiens
<220> FEATURE:
<223> OTHER INFORMATION: human germline heavy chain variable region VH1
      1-02

```
<400> SEQUENCE: 10

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Tyr
             20                  25                  30

Tyr Met His Trp Val Arg Gln Ala Pro Gly Gln Gly Leu Glu Trp Met
         35                  40                  45

Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
             85                  90                  95

Ala Arg

<210> SEQ ID NO 11
<211> LENGTH: 119
<212> TYPE: PRT
<213> ORGANISM: Artificial Sequence
<220> FEATURE:
<223> OTHER INFORMATION: synthetic anti-granulocyte macrophage colony
      stimulating factor (GM-CSF) antibody heavy chain
      variable region (V-H) VH#1

<400> SEQUENCE: 11

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Tyr
             20                  25                  30

Tyr Met His Trp Val Arg Gln Ala Pro Gly Gln Gly Leu Glu Trp Met
         35                  40                  45

Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
             85                  90                  95

Val Arg Arg Asp Arg Phe Pro Tyr Tyr Phe Asp Tyr Trp Gly Gln Gly
            100                 105                 110

Thr Leu Val Thr Val Ser Ser
        115

<210> SEQ ID NO 12
<211> LENGTH: 98
<212> TYPE: PRT
<213> ORGANISM: Homo sapiens
<220> FEATURE:
<223> OTHER INFORMATION: human germline heavy chain variable region VH1
      1-03

<400> SEQUENCE: 12

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
             20                  25                  30

Ala Met His Trp Val Arg Gln Ala Pro Gly Gln Arg Leu Glu Trp Met
         35                  40                  45

Gly Trp Ile Asn Ala Gly Asn Gly Asn Thr Lys Tyr Ser Gln Lys Phe
 50                  55                  60
```

```
Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 13
<211> LENGTH: 119
<212> TYPE: PRT
<213> ORGANISM: Artificial Sequence
<220> FEATURE:
<223> OTHER INFORMATION: synthetic anti-granulocyte macrophage colony
      stimulating factor (GM-CSF) antibody heavy chain
      variable region (V-H) VH#2

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asn Tyr
                20                  25                  30

Tyr Ile His Trp Val Arg Gln Ala Pro Gly Gln Arg Le

<210> SEQ ID NO 15
<211> LENGTH: 119
<212> TYPE: PRT
<213> ORGANISM: Artificial Sequence
<220> FEATURE:
<223> OTHER INFORMATION: synthetic anti-granulocyte macrophage colony
      stimulating factor (GM-CSF) antibody heavy chain
      variable region (V-H) VH#4

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asn Tyr
            20                  25                  30

Tyr Ile His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Ala Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Val Arg Arg Gln Arg Phe Pro Tyr Tyr Phe Asp Tyr Trp Gly Gln Gly
            100                 105                 110

Thr Leu Val Thr Val Ser Ser
        115

<210> SEQ ID NO 16
<211> LENGTH: 119
<212> TYPE: PRT
<213> ORGANISM: Artificial Sequence
<220> FEATURE:
<223> OTHER INFORMATION: synthetic anti-granulocyte macrophage colony
      stimulating factor (GM-CSF) antibody heavy chain
      variable region (V-H) VH#5

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asn Tyr
            20                  25                  30

Tyr Ile His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Val Arg Arg Gln Arg Phe Pro Tyr Tyr Phe Asp Tyr Trp Gly Gln Gly
            100                 105                 110

Thr Leu Val Thr Val Ser Ser
        115

<210> SEQ ID NO 17
<211> LENGTH: 96
<212> TYPE: PRT
<213> ORGANISM: Homo sapiens
<220> FEATURE:
<223> OTHER INFORMATION: human germline kappa light chain variable region VKIII A27

<400> SEQUENCE: 17

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

<210> SEQ ID NO 18
<211> LENGTH: 107
<212> TYPE: PRT
<213> ORGANISM: Artificial Sequence
<220> FEATURE:
<223> OTHER INFORMATION: synthetic anti-granulocyte macrophage colony
      stimulating factor (GM-CSF) antibody kappa light
      chain variable region (V-L) VK#1

<400> SEQUENCE: 18

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Gly Thr Asn
            20                  25                  30

Val Ala Trp Tyr Gln Gln Lys Pro Gly Gln Ala Pro Arg Val Leu Ile
        35                  40                  45

Tyr Ser Thr Ser Ser Arg Ala Thr Gly Ile Thr Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Phe Asn Arg Ser Pro Leu
                85                  90                  95

Thr Phe Gly Gly Gly Thr Lys Val Glu Ile Lys
            100                 105

<210> SEQ ID NO 19
<211> LENGTH: 107
<212> TYPE: PRT
<213> ORGANISM: Artificial Sequence
<220> FEATURE:
<223> OTHER INFORMATION: synthetic anti-granulocyte macrophage colony
      stimulating factor (GM-CSF) antibody kappa light
      chain variable region (V-L) VK#2

<400> SEQUENCE: 19

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Gly Thr Asn
            20                  25                  30

Val Ala Trp Tyr Gln Gln Lys Pro Gly Gln Ala Pro Arg Val Leu Ile
        35                  40                  45

Tyr Ser Thr Ser Ser Arg Ala Thr Gly Ile Thr Asp Arg Phe Ser Gly
    50                  55                  60

Ser Gly Ser Gly Thr Asp Phe Thr Leu Thr Ile Ser Arg Leu Glu Pro

```
                         65                  70                  75                  80
Glu Asp Phe Ala Val Tyr Tyr Cys Gln Gln Phe Asn Lys Ser Pro Leu
                    85                  90                  95

Thr Phe Gly Gly Gly Thr Lys Val Glu Ile Lys
            100                 105

<210> SEQ ID NO 20
<211> LENGTH: 107
<212> TYPE: PRT
<213> ORGANISM: Artificial Sequence
<220> FEATURE:
<223> OTHER INFORMATION: synthetic anti-granulocyte macrophage colony
      stimulating factor (GM-CSF) antibody kappa light
      chain variable region (V-L) VK#3

<400> SEQUENCE: 20

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Ile Gly Ser Asn
            20                  25                  30

Leu Ala Trp Tyr Gln Gln Lys Pro Gly Gln Ala Pro Arg Val Leu Ile
        35                  40                  45

Tyr Ser Thr Ser Ser Arg Ala Thr Gly Ile Thr Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Phe Asn Arg Ser Pro Leu
                    85                  90                  95

Thr Phe Gly Gly Gly Thr Lys Val Glu Ile Lys
            100                 105

<210> SEQ ID NO 21
<211> LENGTH: 107
<212> TYPE: PRT
<213> ORGANISM: Artificial Sequence
<220> FEATURE:
<223> OTHER INFORMATION: synthetic anti-granulocyte macrophage colony
      stimulating factor (GM-CSF) antibody kappa light
      chain variable region (V-L) VK#4

<400> SEQUENCE: 21

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Ile Gly Ser Asn
            20                  25                  30

Leu Ala Trp Tyr Gln Gln Lys Pro Gly Gln Ala Pro Arg Val Leu Ile
        35                  40                  45

Tyr Ser Thr Ser Ser Arg Ala Thr Gly Ile Thr Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Phe Asn Lys Ser Pro Leu
                    85                  90                  95

Thr Phe Gly Gly Gly Thr Lys Val Glu Ile Lys
            100                 105

<210> SEQ ID NO 22
<211> LENGTH: 5
<212> TYPE: PRT
<213> ORGANISM: Artificial Sequence
<220> FEATURE:
```

```
<223>  OTHER INFORMATION: synthetic murine anti-granulocyte macrophage
       colony stimulating factor (GM-CSF) chimeric
       antibody c19/2 heavy chain variable region (V-H)
       complementarity-determining region 1 (CDRH1)

<400>  SEQUENCE: 22

Asp Tyr Asn Ile His
 1               5

<210>  SEQ ID NO 23
<211>  LENGTH: 17
<212>  TYPE: PRT
<213>  ORGANISM: Artificial Sequence
<220>  FEATURE:
<223>  OTHER INFORMATION: synthetic murine anti-granulocyte macrophage
       colony stimulating factor (GM-CSF) chimeric
       antibody c19/2 heavy chain variable region (V-H)
       complementarity-determining region 2 (CDRH2)

<400>  SEQUENCE: 23

Tyr Ile Ala Pro Tyr Ser Gly Gly Thr Gly Tyr Asn Gln Glu Phe Lys
 1               5                  10                  15

Asn

<210>  SEQ ID NO 24
<211>  LENGTH: 11
<212>  TYPE: PRT
<213>  ORGANISM: Artificial Sequence
<220>  FEATURE:
<223>  OTHER INFORMATION: synthetic murine anti-granulocyte macrophage
       colony stimulating factor (GM-CSF) chimeric
       antibody c19/2 light chain variable region (V-L)
       complementarity-determining region 1 (CDRL1)

<400>  SEQUENCE: 24

Lys Ala Ser Gln Asn Val Gly Ser Asn Val Ala
 1               5                  10

<210>  SEQ ID NO 25
<211>  LENGTH: 7
<212>  TYPE: PRT
<213>  ORGANISM: Artificial Sequence
<220>  FEATURE:
<223>  OTHER INFORMATION: synthetic murine anti-granulocyte macrophage
       colony stimulating factor (GM-CSF) chimeric
       antibody c19/2 light chain variable region (V-L)
       complementarity-determining region 2 (CDRL2)

<400>  SEQUENCE: 25

Ser Ala Ser Tyr Arg Ser Gly
 1               5

<210>  SEQ ID NO 26
<211>  LENGTH: 9
<212>  TYPE: PRT
<213>  ORGANISM: Artificial Sequence
<220>  FEATURE:
<223>  OTHER INFORMATION: synthetic murine anti-granulocyte macrophage
       colony stimulating factor (GM-CSF) chimeric
       antibody c19/2 light chain variable region (V-L)
       complementarity-determining region 3 (CDRL3)

<400>  SEQUENCE: 26

Gln Gln Phe Asn Arg Ser Pro Leu Thr
 1               5

<210>  SEQ ID NO 27
<211>  LENGTH: 6
<212>  TYPE: PRT
```

```
<213> ORGANISM: Artificial Sequence
<220> FEATURE:
<223> OTHER INFORMATION: synthetic humaneered anti-granulocyte
      macrophage colony stimulating factor (GM-CSF) antibody heavy
      chain variable region (V-H)
      complementarity-determining region 3 (CDRH3)
<221> NAME/KEY: VARIANT
<222> LOCATION: (2)...(2)
<223> OTHER INFORMATION: Xaa = Gln or Asp

<400> SEQUENCE: 27

Arg Xaa Arg Phe Pro Tyr
 1               5

<210> SEQ ID NO 28
<211> LENGTH: 21
<212> TYPE: PRT
<213> ORGANISM: Artificial Sequence
<220> FEATURE:
<223> OTHER INFORMATION: synthetic anti-granulocyte macrophage colony
      stimulating factor (GM-CSF) antibody heavy chain variable region
      (V-H) complementarity determining region 3 (CDRH3) binding
      specificity determinant (BSD) and complete human J4 germ-line
      J-segment (CDRH3-F4)
<221> NAME/KEY: VARIANT
<222> LOCATION: (2)...(2)
<223> OTHER INFORMATION: Xaa = Gln or Asp

<400> SEQUENCE: 28

Arg Xaa Arg Phe Pro Tyr Tyr Phe Asp Tyr Trp Gly Gln Gly Thr Leu
 1               5                  10                  15

Val Thr Val Ser Ser
                20

<210> SEQ ID NO 29
<211> LENGTH: 5
<212> TYPE: PRT
<213> ORGANISM: Artificial Sequence
<220> FEATURE:
<223> OTHER INFORMATION: synthetic anti-granulocyte macrophage colony
      stimulating factor (GM-CSF) antibody heavy chain
      variable region (V-H) complementarity-determining
      region 1 (CDR1)

<400> SEQUENCE: 29

Gly Tyr Tyr Met His
 1               5

<210> SEQ ID NO 30
<211> LENGTH: 5
<212> TYPE: PRT
<213> ORGANISM: Artificial Sequence
<220> FEATURE:
<223> OTHER INFORMATION: synthetic anti-granulocyte macrophage colony
      stimulating factor (GM-CSF) antibody heavy chain
      variable region (V-H) complementarity-determining
      region 1 (CDR1)

<400> SEQUENCE: 30

Asn Tyr Tyr Ile His
 1               5

<210> SEQ ID NO 31
<211> LENGTH: 17
<212> TYPE: PRT
<213> ORGANISM: Artificial Sequence
<220> FEATURE:
<223> OTHER INFORMATION: synthetic anti-granulocyte macrophage colony
      stimulating factor (GM-CSF) antibody heavy chain
      variable region (V-H) complementarity-determining
      region 2 (CDR2)
```

```
<400> SEQUENCE: 31

Trp Ile Asn Pro Asn Ser Gly Gly Thr Asn Tyr Ala Gln Lys Phe Gln
1               5                   10                  15

Gly

<210> SEQ ID NO 32
<211> LENGTH: 17
<212> TYPE: PRT
<213> ORGANISM: Artificial Sequence
<220> FEATURE:
<223> OTHER INFORMATION: synthetic anti-granulocyte macrophage colony
      stimulating factor (GM-CSF) antibody heavy chain
      variable region (V-H) complementarity-determining
      region 2 (CDR2)

<400> SEQUENCE: 32

Trp Ile Asn Ala Gly Asn Gly Asn Thr Lys Tyr Ser Gln Lys Phe Gln
1               5                   10                  15

Gly

<210> SEQ ID NO 33
<211> LENGTH: 19
<212> TYPE: PRT
<213> ORGANISM: Artificial Sequence
<220> FEATURE:
<223> OTHER INFORMATION: synthetic anti-granulocyte macrophage colony
      stimulating factor (GM-CSF) antibody light chain variable region
      (V-L) complementarity determining region 3 (CDRL3) binding
      specificity determinant (BSD) and complete human JK4 germ-line
      J-segment (CDRL3-F4)

<400> SEQUENCE: 33

Gln Gln Phe Asn Arg Ser Pro Leu Thr Phe Gly Gly Gly Thr Lys Val
1               5                   10

```
<210> SEQ ID NO 36
<211> LENGTH: 11
<212> TYPE: PRT
<213> ORGANISM: Artificial Sequence
<220> FEATURE:
<223> OTHER INFORMATION: synthetic anti-granulocyte macrophage colony
      stimulating factor (GM-CSF) antibody kappa light
      chain variable region (V-L)
      complementarity-determining region 1 (CDR1)

<400> SEQUENCE: 36

Arg Ala Ser Gln Ser Ile Gly Ser Asn Leu Ala
 1               5                  10

<210> SEQ ID NO 37
<211> LENGTH: 7
<212> TYPE: PRT
<213> ORGANISM: Artificial Sequence
<220> FEATURE:
<223> OTHER INFORMATION: synthetic anti-granulocyte macrophage colony
      stimulating factor (GM-CSF) antibody kappa light
      chain variable region (V-L)
      complementarity-determining region 2 (CDR2)

<400> SEQUENCE: 37

Ser Thr Ser Ser Arg Ala Thr
 1               5

<210> SEQ ID NO 38
<211> LENGTH: 10
<212> TYPE: PRT
<213> ORGANISM: Artificial Sequence
<220> FEATURE:
<223> OTHER INFORMATION: synthetic anti-granulocyte macrophage colony
      stimulating factor (GM-CSF) antibody kappa light chain variable
      region (V-L) complementarity-determining region 3 and framework 4
      (F4) region (CDR3-F4)

<400> SEQUENCE: 38

Phe Gly Gly Gly Thr Lys Val Glu Ile Lys
 1               5                  10
```

METHODS OF TREATING HEART FAILURE USING AN ANTI-GM-CSF ANTIBODY

CROSS-REFERENCE TO RELATED APPLICATIONS

This applications claims benefit of Provisional Patent Application Ser. No. 61/043,026, filed Apr. 7, 2008, which is herein incorporated by reference.

BACKGROUND OF THE INVENTION

Left ventricular remodeling that occurs following an ischemic episode such as an acute myocardial infarction, or subsequent to other damage to the myocardium, can lead to heart failure, which is a leading cause of morbidity and mortality in many parts of the world.

Granulocyte macrophage colony stimulating factor (GM-CSF) is a pro-inflammatory cytokine that may play a role in the process of blood vessel formation in patients with coronary artery disease (Seiler et al., Circulation 104:2012-2017, 2001). It has been suggested that GM-CSF induces neovascularization in the heart (see, e.g., U.S. Patent Application Publication No. 20050233992) However, the role of GM-CSF in cardiac re-modeling is unclear. Physical training in patients with congestive heart failure can reduce serum levels of GM-CSF while increasing exercise tolerance (Adamopoulos, et al., Eur. Heart J. 22:791-797, 2001). Further, in a rat model of left ventricular remodeling, treatment with romurtide, which induces GM-CSF, caused expansion of the damaged area (Maekawa et al., J. Amer. Coll. Cardiol. 44:1510-1520, 2004). GM-CSF receptor has also been detected on cardiomycoytes from end-stage heart failure patients (Postiglione et al., Eur. J. Heart Failure 8:564-570, 2006).

This invention is based, in part, on the discovery that neutralization of GM-CSF reduces cardiac damage that results from ischemia, e.g., acute myocardial infarction, and improves ventricular function.

BRIEF SUMMARY OF THE INVENTION

This invention is based on the discovery that a GM-CSF antagonist can be used to treat or prevent heart failure. Accordingly, the invention provides a method of treating a patient that has heart failure, is at risk for heart failure subsequent to an ischemic episode, or has a cardiomyopathy, the method comprising administering a therapeutically effective amount of a GM-CSF antagonist to the patient. In some embodiments, the invention provides a method for treating a patient that has heart failure, wherein the failure is the result of the patient having had an acute myocardial infarction. In some embodiments, a GM-CSF antagonist is administered within twenty four hours of having the acute myocardial infarction. In some embodiments, the patient has Class II, Class III, or Class IV heart failure as determined with reference to the New York Heart Association functional classification. In some embodiments, the patient is being treated with an angiotensin-converting enzyme (ACE) inhibitor.

In some embodiments, the GM-CSF antagonist used in the treatment methods of the invention is an anti-GM-CSF antibody. The antibody can be, for example, a monoclonal antibody, a nanobody or a camellid antibody. In embodiments, the antibody is an antibody fragment that is a Fab, a Fab', a F(ab')2, a scFv, or a dAB, with some embodiments having the antibody fragment conjugated to polyethylene glycol. In some embodiments, the antibody has an affinity of about 100 pM to about 10 nM. In some embodiments the antibody has an affinity of about 0.5 pM to about 100 pM. In some embodiments, the antibody is a neutralizing antibody. In some embodiments, the antibody is a recombinant or chimeric antibody. The antibody can comprise a human variable region. In some embodiments, the antibody comprises a human light chain constant region. In some embodiments, the antibody comprises a human heavy chain constant region, such as a gamma chain. In some embodiments, the antibody binds to the same epitope as chimeric 19/2. In some embodiments, the antibody comprises the $V_H$ and $V_L$ regions of chimeric 19/2. In some embodiments, the antibody comprises a human heavy chain constant region, such as a gamma region. In some embodiments, the antibody comprises the $V_H$ region and $V_L$ region CDR1, CDR2, and CDR3 of chimeric 19/2. In some embodiments, the antibody comprises the $V_H$ region CDR3 and $V_L$ region CDR3 of chimeric 19/2.

In some embodiments, an anti-GM-CSF antibody for use in the invention, comprises a $V_H$ region that comprises a CDR3 binding specificity determinant RQRFPY (SEQ ID NO:3) or RDRFPY (SEQ ID NO:4), a J segment, and a V-segment, wherein the J-segment comprises at least 95% identity to human JH4 (YFDYWGQGTLVTVSS; SEQ ID NO:5) and the V-segment comprises at least 90% identity to a human germ line VH1 1-02 or VH1 1-03 sequence; or a $V_H$ region that comprises a CDR3 binding specificity determinant RQRFPY (SEQ ID NO:3). In some embodiments, the J segment comprises YFDYWGQGTLVTVSS (SEQ ID NO:5). In some embodiments, the CDR3 comprises RQRF-PYYFDY (SEQ ID NO:6) or RDRFPYYFDY (SEQ ID NO:7). In some embodiments, the $V_H$ region CDR1 is a human germline VH1 CDR1; the $V_H$ regions CDR2 is a human germline VH1 CDR2; or both the CDR1 and CDR2 are from a human germline VH1 sequence. In some embodiments, the $V_H$ comprises a $V_H$ CDR1, or a $V_H$ CDR2, or both a $V_H$ CDR1 and a $V_H$ CDR2 as shown in a $V_H$ region set forth in FIG. 9. In some embodiments, the V-segment sequence has a $V_H$ V segment sequence shown in FIG. 9. In additional embodiments, the $V_H$ of the anti-GM-CSF antibody has the sequence of VH#1, VH#2, VH#3, VH#4, or VH#5 set forth in FIG. 9.

In some embodiments, an anti-GM-CSF antibody for use in the invention comprises a $V_L$ region that comprises a CDR3 comprising the amino acid sequence FNK or FNR. In some embodiments, the $V_L$ region comprises a human germline JK4 region. In some embodiments, the $V_L$ region CDR3 comprises QQFN(K/R)SPLT (SEQ ID NO:8). In some embodiments, the $V_L$ region comprises a CDR1, or a CDR2, or both a CDR1 and CDR2 of a sequence $V_L$ region shown in FIG. 9. In some embodiments the $V_L$ region comprises a V segment that has at least 95% identity to the VKIIIA27 V-segment sequence as shown in FIG. 9. In some embodiments, the $V_L$ region has the sequence of VK#1, VK#2, VK#3, or VK#4 set forth in FIG. 9.

In some embodiments, the anti-GM-CSF antibody for use in the invention comprises a $V_L$ region that comprises a CDR3 that comprises QQFNKSPLT (SEQ ID NO:9).

In some embodiments, an anti-GM-CSF for use in the invention comprises a $V_H$ region where the $V_H$ CDR3 comprises a CDR3 binding specificity determinant RQRFPY (SEQ ID NO:3) or RDRFPY (SEQ ID NO:4); and a $V_L$ region where the $V_L$ CDR 3 comprises QQFNKSPLT (SEQ ID NO:9).

In some embodiments, the anti-GM-CSF $V_H$ region or the $V_L$ region, or both the $V_H$ and $V_L$ region amino acid sequences comprise a methionine at the N-terminus.

In some embodiments, the antibody is a human antibody. In some embodiments, the antibody has a half-life of about 7 to about 25 days. In some embodiments, the antibody is administered at a dose between about 1 mg/kg of body weight and about 10 mg/kg of body weight.

The GM-CSF antagonist used in the methods of the invention can be administered using a variety of methods, including by injection. In some embodiments, the GM-CSF antagonist is administered intravenously. In some embodiments, the GM-CSF antagonist is administered subcutaneously. In some embodiments, the GM-CSF antagonist is administered intramuscularly. In some embodiments, the GM-CSF antagonist is administered multiple times. In some embodiments, the GM-CSF antagonist is an anti-GM-CSF receptor antibody, a soluble GM-CSF receptor, a cytochrome b562 antibody mimetic, an adnectin, a lipocalin scaffold antibody mimetic, a calixarene antibody mimetic, or an antibody like binding peptidomimetic.

A patient that can be treated with a GM-CSF antagonist, e.g., an anti-GM-CSF antibody, in accordance with the invention includes any patient further described hereinbelow.

BRIEF DESCRIPTION OF THE DRAWINGS

FIG. 9 provides exemplary $V_H$ (SEQ ID NOS:11 and 13-16) and $V_L$ (SEQ ID NOS:18-21) sequences of anti-GM-CSF antibodies. VH1 1-02=SEQ ID NO:10; VH1 1-03=SEQ ID NO:12; VH#1=SEQ ID NO:11; VH#2=SEQ ID NO:13; VH#3=SEQ ID NO:14; VH#4=SEQ ID NO:15; VH#5=SEQ ID NO:16; VKIII A27=SEQ ID NO:17; VK#1=SEQ ID NO:18; VK#2=SEQ ID NO:19; VK#3=SEQ ID NO:20; VK#4=SEQ ID NO:21.

DETAILED DESCRIPTION OF THE INVENTION

Definitions

Figure 1:
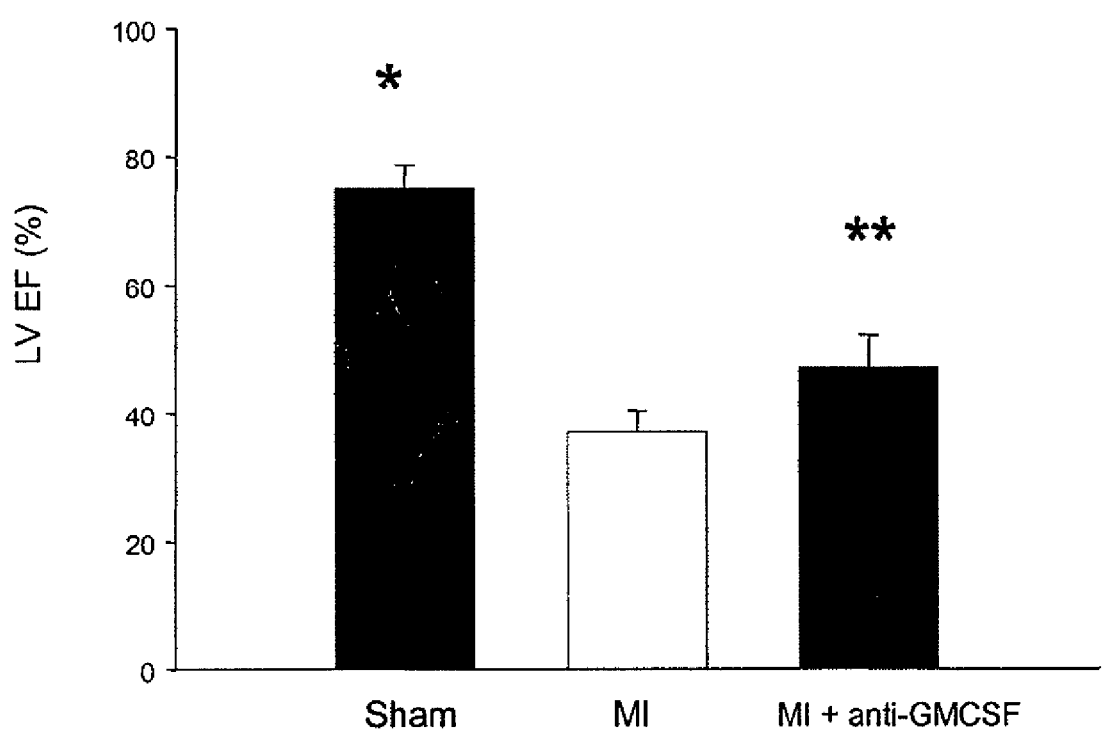
FIG. 1 provides data showing the effects of anti-GM-CSF antibody on global left ventricular function, as assessed by left ventricular ejection fractions (LVEF), in infarcted rats. The graph shows the mean LVEF (%)±standard error (SE) among treated groups. Sham (N=5), MI (N=10), MI+anti-GM-CSF (N=12). * P<0.05 vs all groups  P<0.05 vs MI and Sham FIG. 2** provides data showing the left ventricular (LV) systolic pressure in animals subject to myocardial infarction (MI) that are treated with GM-CSF antibody in comparison to untreated MI animals.

As used herein, "congestive heart failure" or "heart failure" refers to a condition where the heart fails to pump a sufficient volume of blood through the circulatory system to support adequate tissue perfusions. Heart failure often results from one or more episodes of ischemia, such as an acute myocardial infarction, where a patient suffers damage to cardiac tissue, or from some other cause of cardiomyopathy.

"Cardiomyopathy" as used herein refers to damage and/or weakening of the heart muscle. Cardiomyopathy can result from infection as well as other disorders, including exposure to toxic compounds such as chemotherapeutic agents, electroloyte imbalances, hypertension, and various genetic disorders. Heart failure results when there is a reduction in cardiac function and the ability to pump blood. In "dilated cardiomyopathy", previously normal heart muscle becomes damaged, leading to a generalized weakening of the walls of the cardiac chambers A patient that has "heart failure" is a patient that has suffered a loss in the ability to pump blood. Diagnosis is based on at least one of the diagnostic systems used in the art, e.g., the Framingham criteria, the Boston criteria, or the Duke criteria.

A patient "at risk for heart failure" in the context of this invention refers to a patient who has not been diagnosed with heart failure, but who has suffered one or more ischemic event or suffers from a cardiomyopathy that can lead to heart failure. An ischemic event may be an acute ischemic episode, such as a myocardial infarction, or a transient ischemic episode.

An "ischemic episode" or "ischemia" as used herein refers to inadequate blood supply (circulation) to a local area due to blockage of the blood vessels to the area. The loss of circulation to the area may be complete or partial. An "ischemic episode" includes situations such as acute myocardial infarction as well as chronic ischemia, e.g., due to partial blockage of an artery as a result of coronary artery disease, or transient ischemic episodes, e.g., angina attacks, which typically last from 1 to 15 minutes.

As used herein, "a therapeutic agent for the treatment or prevention of heart failure" refers to an agent, e.g., a GM-CSF antagonist such as an anti-GM-CSF antibody, that when administered to a patient suffering from heart failure, or who is at risk for heart failure, e.g., due to an acute myocardial infarction, at least partially reduces or slows symptoms of heart failure and complications associated with heart failure; or delays or prevents the onset of symptoms of heart failure. Such an agent reduces or prevents structural changes to the heart, e.g., left ventricular remodeling, that can lead to heart failure.

As used herein, "Granulocyte Macrophage-Colony Stimulating Factor" (GM-CSF) refers to a small naturally occurring glycoprotein with internal disulfide bonds having a molecular weight of approximately 23 kDa. In humans, it is encoded by a gene located within the cytokine cluster on human chromosome 5. The sequence of the human gene and protein are known. The protein has an N-terminal signal sequence, and a C-terminal receptor binding domain (Rasko and Gough In: The Cytokine Handbook, A. Thomson, et al, Academic Press, New York (1994) pages 349-369). Its three-dimensional structure is similar to that of the interleukins, although the amino acid sequences are not similar. GM-CSF is produced in response to a number of inflammatory mediators present in the hemopoietic environment and at peripheral sites of inflammation. GM-CSF is able to stimulate the production of neutrophilic granulocytes, macrophages, and mixed granulocyte-macrophage colonies from bone marrow cells and can stimulate the formation of eosinophil colonies from fetal liver progenitor cells. GM-CSF can also stimulate some functional activities in mature granulocytes and macrophages and inhibits apoptosis of granulocytes and macrophages.

The term "granulocyte macrophage-colony stimulating factor receptor" (GM-CSFR)" refers to a membrane bound receptor expressed on cells that transduces a signal when bound to granulocyte macrophage colony-stimulating factor (GM-CSF). GM-CSFR consists of a ligand-specific low-affinity binding chain (GM-CSFR alpha) and a second chain that is required for high-affinity binding and signal transduction. This second chain is shared by the ligand-specific alpha-chains for the interleukin 3 (IL-3) and IL-5 receptors and is therefore called beta common (beta-c or βc). The cytoplasmic region of GM-CSFR alpha consists of a membrane-proximal conserved region shared by the alpha 1 and alpha 2 isoforms and a C-terminal variable region that is divergent between alpha 1 and alpha 2. The cytoplasmic region of beta-c contains membrane proximal serine and acidic domains that are important for the proliferative response induced by GM-CSF The term "soluble granulocyte macrophage-colony stimulating factor receptor" (sGM-CSFR) refers to a non-membrane bound receptor that binds GM-CSF, but does not transduce a signal when bound to the ligand.

As used herein, "GM-CSF antagonist" refers to a molecule or compound that interacts with GM-CSF, or its receptor, to reduce or block (either partially or completely) signal transduction that would otherwise result from the binding of GM-CSF to its cognate receptor expressed on cells. GM-CSF antagonists may act by reducing the amount of GM-CSF ligand available to bind the receptor (e.g., antibodies that once bound to GM-CSF increase the clearance rate of GM-CSF) or prevent the ligand from binding to its receptor either by binding to GM-CSF or the receptor (e.g., neutralizing antibodies). GM-CSF antagonist may also include inhibitors, which may include compounds that bind GM-CSF or its receptor to partially or completely inhibit signaling. GM-CSF antagonist may include antibodies, natural or synthetic ligands or fragments thereof, polypeptides, small molecules, and the like.

A "purified" GM-CSF antagonist as used herein refers to a GM-CSF antagonist that is substantially or essentially free from components that normally accompany it as found in its native state. For example, a GM-CSF antagonist such as an anti-GM-CSF antibody, that is purified from blood or plasma is substantially free of other blood or plasma components such as other immunoglobulin molecules. Purity and homogeneity are typically determined using analytical chemistry techniques such as polyacrylamide gel electrophoresis or high performance liquid chromatography. A protein that is the predominant species present in a preparation is substantially purified. Typically, "purified" means that the protein is at least 85% pure, more preferably at least 95% pure, and most preferably at least 99% pure relative to the components with which the protein naturally occurs.

As used herein, an "antibody" refers to a protein functionally defined as a binding protein and structurally defined as comprising an amino acid sequence that is recognized by one of skill as being derived from the framework region of an immunoglobulin-encoding gene of an animal that produces antibodies. An antibody can consist of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains, respectively.

The term "antibody" as used herein also includes antibody fragments that retain binding specificity. For example, there are a number of well characterized antibody fragments. Thus, for example, pepsin digests an antibody C-terminal to the disulfide linkages in the hinge region to produce F(ab')2, a dimer of Fab which itself is a light chain joined to VH-CH1 by a disulfide bond. The F(ab')2 may be reduced under mild conditions to break the disulfide linkage in the hinge region thereby converting the (Fab')2 dimer into a Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that fragments can be synthesized de novo by utilizing recombinant DNA methodology or chemically. Thus, the term "antibody", as used here includes antibody fragments either produced by the modification of whole antibodies or synthesized using recombinant DNA methodologies.

Antibodies as used here also include various $V_H$-$V_L$ pair formats, including single chain antibodies (antibodies that exist as a single polypeptide chain), e.g., single chain Fv antibodies (sFv or scFv), in which a variable heavy and a variable light region are joined together (directly or through a peptide linker) to form a continuous polypeptide. The single chain Fv antibody is a covalently linked $V_H$-$V_L$ that may be expressed from a nucleic acid including $V_H$- and $V_L$-encoding sequences either joined directly or joined by a peptide-encoding linker (e.g., Huston, et al. *Proc. Nat. Acad. Sci. USA*, 85:5879-5883, 1988). While the $V_H$ and $V_L$ are connected to each as a single polypeptide chain, the $V_H$ and $V_L$ domains associate non-covalently. An antibody can also be in another fragment form, such as a disulfide-stabilized Fv (dsFv). Other fragments can also be generated, e.g., using recombinant techniques, as soluble proteins or as fragments obtained from display methods. Antibodies can also include diantibodies and miniantibodies.

Antibodies of the invention also include heavy chain dimers, such as antibodies from camelids. Since the $V_H$ region of a heavy chain dimer IgG in a camelid does not have to make hydrophobic interactions with a light chain, the region in the heavy chain that normally contacts a light chain is changed to hydrophilic amino acid residues in a camelid. $V_H$ domains of heavy-chain dimer IgGs are called VHH domains. Antibodies for use in the current invention additionally include single domain antibodies (dAbs) and nanobodies (see, e.g., Cortez-Retamozo, et al., *Cancer Res.* 64:2853-2857, 2004).

As used herein, "V-region" refers to an antibody variable region domain comprising the segments of Framework 1, CDR1, Framework 2, CDR2, and Framework 3, including CDR3 and Framework 4, which segments are added to the V-segment as a consequence of rearrangement of the heavy chain and light chain V-region genes during B-cell differentiation.

As used herein, "complementarity-determining region (CDR)" refers to the three hypervariable regions in each chain that interrupt the four "framework" regions established by the light and heavy chain variable regions. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, for example, a $V_H$ CDR3 is located in the variable domain of the heavy chain of the antibody in which it is found, whereas a $V_L$ CDR1 is the CDR1 from the variable domain of the light chain of the antibody in which it is found.

The sequences of the framework regions of different light or heavy chains are relatively conserved within a species. The framework region of an antibody, that is the combined framework regions of the constituent light and heavy chains, serves to position and align the CDRs in three dimensional space.

The amino acid sequences of the CDRs and framework regions can be determined using various well known definitions in the art, e.g., Kabat, Chothia, international ImMunoGeneTics database (IMGT), and AbM (see, e.g., Johnson et al., supra; Chothia & Lesk, 1987, Canonical structures for the hypervariable regions of immunoglobulins. *J. Mol. Biol.* 196, 901-917; Chothia et al., 1989, Conformations of immunoglobulin hypervariable regions. *Nature* 342, 877-883; Chothia et al., 1992, structural repertoire of the human VH segments *J. Mol. Biol.* 227, 799-817; Al-Lazikani et al., *J. Mol. Biol.* 1997, 273(4)). Definitions of antigen combining sites are also described in the following: Ruiz et al., IMGT, the international ImMunoGeneTics database. *Nucleic Acids Res.*, 28, 219-221 (2000); and Lefranc, M.-P. IMGT, the international ImMunoGeneTics database. *Nucleic Acids Res.* January 1; 29(1):207-9 (2001); MacCallum et al, Antibody-antigen interactions: Contact analysis and binding site topography, *J. Mol. Biol.*, 262 (5), 732-745 (1996); and Martin et al, *Proc. Natl. Acad. Sci. USA*, 86, 9268-9272 (1989); Martin, et al, *Methods Enzymol.*, 203, 121-153, (1991); Pedersen et al, *Immunomethods*, 1, 126, (1992); and Rees et al, In Sternberg M. J. E. (ed.), Protein Structure Prediction. Oxford University Press, Oxford, 141-172 1996).

"Epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

As used herein, "neutralizing antibody" refers to an antibody that binds to GM-CSF and prevents signaling by the GM-CSF receptor, or inhibits binding of GM-CSF to its receptor.

As used herein, "chimeric antibody" refers to an immunoglobulin molecule in which (a) the constant region, or a portion thereof, is altered, replaced or exchanged so that the antigen binding site (variable region) is linked to a constant region of a different or altered class, effector function and/or species, or an entirely different molecule that confers new properties to the chimeric antibody, e.g., an enzyme, toxin, hormone, growth factor, drug, etc.; or (b) the variable region, or a portion thereof, is altered, replaced or exchanged with a variable region, or portion thereof, having a different or altered antigen specificity; or with corresponding sequences from another species or from another antibody class or subclass.

As used herein, "humanized antibody" refers to an immunoglobulin molecule in CDRs from a donor antibody are grafted onto human framework sequences. Humanized antibodies may also comprise residues of donor origin in the framework sequences. The humanized antibody can also comprise at least a portion of a human immunoglobulin constant region. Humanized antibodies may also comprise residues which are found neither in the recipient antibody nor in the imported CDR or framework sequences. Humanization can be performed using methods known in the art (e.g., Jones et al., *Nature* 321:522-525; 1986; Riechmann et al., *Nature* 332:323-327, 1988; Verhoeyen et al., *Science* 239:1534-1536, 1988); Presta, *Curr. Op. Struct. Biol.* 2:593-596, 1992; U.S. Pat. No. 4,816,567), including techniques such as "superhumanizing" antibodies (Tan et al., *J. Immunol.* 169: 1119, 2002) and "resurfacing" (e.g., Staelens et al, *Mol. Immunol.* 43: 1243, 2006; and Roguska et al., *Proc. Natl. Acad. Sci. USA* 91: 969, 1994).

A "humaneered" antibody in the context of this invention refers to an engineered human antibody having a binding specificity of a reference antibody. A "humaneered" antibody for use in this invention has an immunoglobulin molecule that contains minimal sequence derived from a donor immunoglobulin. Typically, an antibody is "humaneered" by joining a DNA sequence encoding a binding specificity determinant (BSD) from the CDR3 region of the heavy chain of the reference antibody to human $V_H$ segment sequence and a light chain CDR3 BSD from the reference antibody to a human $V_L$ segment sequence. A "BSD" refers to a CDR3-FR4 region, or a portion of this region that mediates binding specificity. A binding specificity determinant therefore can be a CDR3-FR4, a CDR3, a minimal essential binding specificity determinant of a CDR3 (which refers to any region smaller than the CDR3 that confers binding specificity when present in the V region of an antibody), the D segment (with regard to a heavy chain region), or other regions of CDR3-FR4 that confer the binding specificity of a reference antibody. Methods for humaneering are provided in US patent application publication no. 20050255552 and US patent application publication no. 20060134098.

A "human" antibody as used herein encompasses humanized and humaneered antibodies, as well as human monoclonal antibodies that are obtained using known techniques.

The term "heterologous" when used with reference to portions of a nucleic acid indicates that the nucleic acid comprises two or more subsequences that are not normally found in the same relationship to each other in nature. For instance, the nucleic acid is typically recombinantly produced, having two or more sequences, e.g., from unrelated genes arranged to make a new functional nucleic acid. Similarly, a heterologous protein will often refer to two or more subsequences that are not found in the same relationship to each other in nature.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

The phrase "specifically (or selectively) binds" to an antibody or "specifically (or selectively) immunoreactive with," when referring to a protein or peptide, refers to a binding reaction where the antibody binds to the protein of interest. In the context of this invention, the antibody binds to the antigen of interest, e.g., GM-CSF, with an affinity that is at least 100-fold better than its affinity for other antigens.

The term "equilibrium dissociation constant ($K_D$) refers to the dissociation rate constant ($k_d$, time$^{-1}$) divided by the association rate constant ($k_a$, time$_{-1}$, M$^{-1}$). Equilibrium dissociation constants can be measured using any known method in the art. The antibodies of the present invention are high affinity antibodies. Such antibodies have an affinity better than 500 nM, and often better than 50 nM or 10 nM. Thus, in some embodiments, the antibodies of the invention have an affinity in the range of 500 nM to 100 pM, or in the range of 50 or 25 nM to 100 pM, or in the range of 50 or 25 nM to 50 pM, or in the range of 50 nM or 25 nM to 1 pM.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions, as well as naturally occurring, e.g., polymorphic or allelic variants, and man-made variants. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of one of the number of contiguous positions selected from the group consisting typically of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

Preferred examples of algorithms that are suitable for determining percent sequence identity and sequence similarity include the BLAST and BLAST 2.0 algorithms, which are described in Altschul et al., *Nuc. Acids Res.* 25:3389-3402 (1977) and Altschul et al., *J. Mol. Biol.* 215:403-410 (1990). BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, e.g., for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value;

the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001. Log values may be large negative numbers, e.g., 5, 10, 20, 30, 40, 40, 70, 90, 110, 150, 170, etc.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, e.g., where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequences.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" in some embodiments denotes that a protein gives rise to essentially one band in an electrophoretic gel. Preferably, it means that the protein is at least 85% pure, more preferably at least 95% pure, and most preferably at least 99% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. Typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

I. Introduction

The invention relates to methods of administering a GM-CSF antagonist for the treatment of patients that have heart failure or are at risk for heart failure due to cardiac injury such as an ischemic event, e.g., acute myocardial infarction. The GM-CSF antagonists may include anti-GM-CSF antibodies, anti-GM-CSF receptor antibodies, or other inhibitors that prevent or reduce signaling that normally results from the binding of GM-CSF to its cognate receptor. Many types of GM-CSF antagonists are known (see, e.g., William, in New Drugs for Asthma, Allergy and COPD, Prog. Repir. Res.; Hansel & Barnes, eds, Basel, Karger, 2001 vol 31:251-255; and the references cited therein).

Antibodies, e.g., anti-GM-CSF or anti-GM-CSF receptor antibodies, suitable for use with the present invention may be monoclonal, polyclonal, chimeric, humanized, humaneered, or human. Other GM-CSF antagonists suitable for use with the present invention may include naturally occurring or synthetic ligands (or fragments thereof) that compete with GM-CSF for binding to the receptor, but do not result in signaling when bound to the receptor. Additional non-limiting GM-CSF antagonists may include polypeptides, nucleic acids, small molecules and the like that either partially or completely block signaling that would naturally result from the binding of GM-CSF to its receptor in the absence of the GM-CSF antagonist.

II. Patients with Heart Failure or at Risk for Heart Failure

Patients that can be treated in accordance with the invention have heart failure or are at risk for heart failure. Heart failure can be measured by any number of endpoints. For example, left ventricular ejection fraction (LVEF) is a measure of cardiac functions that is commonly used as a diagnostic endpoint. For the purposes of this patent, the terms "LVEF", "left ventricular ejection fraction", and "ejection fraction" are used interchangeably.

In some embodiments, patients that can be treated with a GM-CSF antagonist as described herein, e.g., an anti-GM-CSF antibody, have systolic heart failure. A normal individual typically has an ejection fraction of about 50% or greater. An ejection fraction less than about 40 percent is indicative of systolic heart failure. Accordingly, in some embodiments, a patient treated with an anti-GM-CSF antagonist may have an ejection fraction of about 40% or less. In other embodiments, patients have diastolic heart failure, in which the ejection fraction may be in the normal range, but the right ventricle does not relax or fill properly, so less blood enters the heart. Patients who are treated in accordance with the invention may have damage to either side of the heart.

Heart failure often occurs as a consequence of one or more ischemic events that damages cardiac tissue. Changes to cardiac structure occur, i.e., left ventricular remodeling, that result in loss of cardiac function. Left ventricular remodeling refers to the changes in the size, shape, and function of the heart after injury. As noted above, the injury is often due to acute myocardial infarction, but can be due to other causes of a cardiomyopathy including bacterial or viral infection, exposure to toxic agents, or as a result of electrolyte imbalance that may occur because of hypertension or endocrine abnormalities. After the injury, a series of histopathological and structural changes that involve the extracellular matrix, collagen, fibrosis, cellular damage and death occur that lead to progressive decline in ventricular performance. Ultimately, left ventricular remodeling may result in diminished contractile function and reduced stroke volume. Not to be bound by theory, a GM-CSF antagonist inhibits re-modeling by reducing the infiltration and activation of tissue macrophages in infarcted tissue.

Commonly used diagnostic systems for heart failure include the "Framingham criteria" (McKee et al., *N. Engl. J. Med.* 285 (26): 1441-6, 1971) (derived from the Framingham Heart Study), the "Boston criteria" (Carlson et al., *J. Chronic Diseases* 38:733-9, 1985) the "Duke criteria" (Harlan et al., *Ann. Intern. Med.* 86:133-8, 1977) and (in the setting of acute myocardial infarction) the "Killip class" (Killip & Kimball, *Am. J. Cardiol.* 20:457-64, 1967). Functional classification is generally done by the New York Heart Association (NYHA) Functional Classification. (Criteria Committee, New York Heart Association. Diseases of the heart and blood vessels. Nomenclature and criteria for diagnosis, 6th ed. Boston: Little, Brown and co, 1964; 114). This score documents severity of symptoms, and can be used to assess response to treatment. The classes (I-IV) are:

Class I: no limitation is experienced in any activities; there are no symptoms from ordinary activities.

Class II: slight, mild limitation of activity; the patient is comfortable at rest or with mild exertion.

Class III: marked limitation of any activity; the patient is comfortable only at rest.

Class IV: any physical activity brings on discomfort and symptoms occur at rest.

In its 2001 guidelines, the American College of Cardiology/American Heart Association working group introduced four stages of heart failure:

Stage A: a high risk for HF in the future but no structural heart disorder;

Stage B: a structural heart disorder but no symptoms at any stage;

Stage C: previous or current symptoms of heart failure in the context of an underlying structural heart problem, but managed with medical treatment;

Stage D: advanced disease requiring hospital-based support, a heart transplant or palliative care.

A GM-CSF antagonist, e.g., an anti-GM-CSF antibody, may be administered to patients in any of these classifications or stages of heart failure. In some embodiments, a GM-CSF antagonist, such as an anti-GM-CSF antibody, is administered to a patient who has NYHA Class II, Class III, or Class IV heart failure.

Patient response to GM-CSF antagonist treatment can be evaluated by monitoring symptoms, as noted above. For example, echocardiography can be employed to measure ejection fraction. In other embodiments, levels of inflammatory cytokines in the blood may be measured. In further embodiments, levels of substances such as C-reactive protein (CRP), which is an indicator of inflammation or other injury, can be determined to assess whether the levels decrease in response to treatment with a GM-CSF antagonist. In some embodiments, levels of a macrophage marker, e.g., neopterin, may be evaluated. A patient that exhibits a therapeutic response to treatment exhibits a reduction of the symptoms of heart failure.

Patients that can be treated with a GM-CSF antagonist in accordance with the invention include patients who are at risk for heart failure, e.g., due to experiencing one or more ischemic events, such as a myocardial infarction. For example, patients who have suffered from a heart attack and/or experienced transient ischemic episodes may be treated with a GM-CSF antagonist, e.g., an anti-GM-CSF antibody. Treatment may be initiated after the ischemic episode, but before the diagnosis of heart failure, or can be initiated after the diagnosis of heart failure.

In other embodiments, a patient who is treated with a GM-CSF antagonist may have a cardiomyopathy, such as dilated cardiomyopathy. In some embodiments, such a patient may have a diagnosis of heart failure. In other embodiments, the patient may not have progressed to heart failure. The cardiomyopathy may originate from any number of causes, including infection, e.g., with a virus, bacteria, *rickettsia*, or a parasite. In other embodiments, the GM-CSF antagonist may be administered to a patient who has a cardiomyopathy that arises from a nutritional disease or a systemic metabolic disease, or hypertension. In other embodiments, the cardiomyopathy may be hypertrophic cardiomyopathy due to genetic disorder or arrhythmogenic right ventricular cardiomyopathy. The GM-CSF antagonist is administered in an amount sufficient to reduce scarring, fibrosis, or other structural rearrangements that can lead to compromised cardiac function. The effects of treatment with a GM-CSF antagonist can be assessed using markers such as levels of inflammatory cytokines, CRP levels and the like. In some embodiments, echocardiography can be employed to examine cardiac structural changes.

In some embodiments, a GM-CSF antagonist is administered to a patient who is not otherwise a candidate for an anti-GM-CSF treatment. In some embodiments, a heart failure patient, and/or a patient that has a cardiomyopathy, who is administered a GM-CSF antagonist in accordance with the invention does not have an acute or chronic inflammatory conditions. In some embodiments, a heart failure patient, and/or a patient that has a cardiomyopathy, who is administered a GM-CSF antagonist in accordance with the invention does not have rheumatoid arthritis, Alzheimer's disease; osteopenia; inflammatory bowel disease; Crohns' disease; type I diabetes; idiopathic thrombocytopenic purpura; multiple sclerosis; psoriasis; temporal arteritis, polyarteritis nodosa, or a chronic inflammatory lung disease such as asthma, chronic bronchitis, emphysema or chronic obstructive airway disease; cancer; including leukemias and lymphoid tumors; systemic lupus erythematosis; polymyalgia rheumatica; or nephritis. In some embodiments, the patient does not have atherosclerosis.

As noted above, the invention provides methods for treating heart failure, by administering a GM-CSF antagonist to a patient. GM-CSF antagonists suitable for use in the invention selectively interfere with the induction of signaling by the GM-CSF receptor, e.g., by causing a reduction in the binding of GM-CSF to the receptor. Such antagonists may include antibodies that bind the GM-CSF receptor, antibodies that bind GM-CSF, and other proteins or small molecules that compete for binding of GM-CSF to its receptor or inhibit signaling that normally results from the binding of the ligand to the receptor, thereby neutralizing GM-CSF activity.

In some embodiments, the GM-CSF antagonist, e.g., purified anti-GM-CSF from human plasma, is purified from a natural source. In many embodiments, the GM-CSF antagonist used in the invention is a recombinant protein, e.g., an anti-GM-CSF antibody; an anti-GM-CSF receptor antibody; a soluble GM-CSF receptor; or a modified GM-CSF polypeptide that competes for binding with GM-CSF to a receptor but is inactive. Recombinant expression technology is widely known in the art. General molecular biology methods, including expression methods, can be found, e.g., in instruction manuals, such as, Sambrook and Russel (2001) Molecular Cloning: A laboratory manual 3rd ed. Cold Spring Harbor Laboratory Press; Current Protocols in Molecular Biology (2006) John Wiley and Sons ISBN: 0-471-50338-X.

A variety of prokaryotic and/or eukaryotic based protein expression systems may be employed to produce a GM-CSF antagonist protein. Many such systems are widely available from commercial suppliers. These include both prokaryotic and eukaryotic expression systems.

GM-CSF Antibodies

In some embodiments, the GM-CSF antagonist is an antibody that binds GM-CSF or an antibody that binds to the GM-CSF receptor α or β subunit. In the context of this invention, the terms "anti-GM-CSF antibody" and "GM-CSF antibody" are used interchangeably to refer to an antibody that specifically binds to GM-CSF. Similarly, an antibody that binds to the GM-CSF receptor α or β subunit may referred to as an "anti-GM-CSF receptor antibody" or a "GM-CSF receptor antibody". The antibodies can be raised against GM-CSF (or GM-CSF receptor) proteins, or fragments, or produced recombinantly. Antibodies to GM-CSF for use in the invention can be neutralizing or can be non-neutralizing antibodies that bind GM-CSF and increase the rate of in vivo clearance of GM-CSF such that the GM-CSF level in the circulation is reduced. Often, the anti-GM-CSF antibody is a neutralizing antibody.

Methods of preparing polyclonal antibodies are known to the skilled artisan (e.g., Harlow & Lane, Antibodies, A Laboratory manual (1988); Methods in Immunology). Polyclonal antibodies can be raised in a mammal by one or more injections of an immunizing agent and, if desired, an adjuvant. The immunizing agent includes a GM-CSF or GM-CSF receptor protein, or fragment thereof.

In some embodiment, an anti-GM-CSF antibody for use in the invention is purified from human plasma. In such embodiments, the anti-GM-CSF antibody is typically a polyclonal antibody that is isolated from other antibodies present in human plasma. Such an isolation procedure can be performed, e.g., using known techniques, such as affinity chromatography.

In some embodiments, the GM-CSF antagonist is a monoclonal antibody. Monoclonal antibodies may be prepared using hybridoma methods, such as those described by Kohler & Milstein, Nature 256:495 (1975). In a hybridoma method, a mouse, hamster, or other appropriate host animal, is typically immunized with an immunizing agent, such as human GM-CSF, to elicit lymphocytes that produce or are capable of producing antibodies that will specifically bind to the immunizing agent. Alternatively, the lymphocytes may be immunized in vitro. The immunizing agent preferably includes human GM-CSF protein, fragments thereof, or fusion protein thereof.

Human monoclonal antibodies can be produced using various techniques known in the art, including phage display libraries (Hoogenboom & Winter, *J. Mol. Biol.* 227:381 (1991); Marks et al., *J. Mol. Biol.* 222:581 (1991)). The techniques of Cole et al. and Boerner et al. are also available for the preparation of human monoclonal antibodies (Cole et al., Monoclonal Antibodies and Cancer Therapy, p. 77 (1985) and Boerner et al., *J. Immunol.* 147(1):86-95 (1991)). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, e.g., in U.S. Pat. Nos. 5,545,807; 5,545,806; 5,569,825; 5,625,126; 5,633,425; 5,661,016, and in the following scientific publications: Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); Lonberg & Huszar, *Intern. Rev. Immunol.* 13:65-93 (1995).

In some embodiments the anti-GM-CSF antibodies are chimeric or humanized monoclonal antibodies. As noted supra, humanized forms of antibodies are chimeric immunoglobulins in which residues from a complementary determining region (CDR) of human antibody are replaced by residues from a CDR of a non-human species such as mouse, rat or rabbit having the desired specificity, affinity and capacity.

An antibody that is employed in the invention can be in any format. For example, in some embodiments, the antibody can be a complete antibody including a constant region, e.g., a human constant region, or can be a fragment or derivative of a complete antibody, e.g., an Fd, a Fab, Fab', F(ab')$_2$, a scFv, an Fv fragment, or a single domain antibody, such as a nanobody or a camelid antibody. Such antibodies may additionally be recombinantly engineered by methods well known to persons of skill in the art. As noted above, such antibodies can be produced using known techniques.

In some embodiments of the invention, the antibody is additionally engineered to reduce immunogenicity, e.g., so that the antibody is suitable for repeat administration. Methods for generating antibodies with reduced immunogenicity include humanization/humaneering procedures and modification techniques such as de-immunization, in which an antibody is further engineered, e.g., in one or more framework regions, to remove T cell epitopes.

In some embodiments, the antibody is a humaneered antibody. A humaneered antibody is an engineered human antibody having a binding specificity of a reference antibody, obtained by joining a DNA sequence encoding a binding specificity determinant (BSD) from the CDR3 region of the heavy chain of the reference antibody to human VH segment sequence and a light chain CDR3 BSD from the reference antibody to a human VL segment sequence. Methods for humaneering are provided in US patent application publication no. 20050255552 and US patent application publication no. 20060134098.

An antibody can further be de-immunized to remove one or more predicted T-cell epitopes from the V-region of an antibody. Such procedures are described, for example, in WO 00/34317.

In some embodiments, the variable region is comprised of human V-gene sequences. For example, a variable region sequence can have at least 80% identity, or at least 85% identity, at least 90% identity, at least 95% identity, at least 96% identity, at least 97% identity, at least 98% identity, or at least 99% identity, or greater, with a human germ-line V-gene sequence.

An antibody used in the invention can include a human constant region. The constant region of the light chain may be a human kappa or lambda constant region. The heavy chain constant region is often a gamma chain constant region, for example, a gamma-1, gamma-2, gamma-3, or gamma-4 constant region.

In some embodiments, e.g., where the antibody is a fragment, the antibody can be conjugated to another molecule, e.g., to provide an extended half-life in vivo such as a polyethylene glycol (pegylation) or serum albumin. Examples of PEGylation of antibody fragments are provided in Knight et al (2004) Platelets 15: 409 (for abciximab); Pedley et al (1994) Br. J. Cancer 70: 1126 (for an anti-CEA antibody) Chapman et al (1999) Nature Biotech. 17: 780.

As understood by one skilled in the art, in some embodiments, e.g., in particular when the GM-CSF antagonist is an antibody that binds to GM-CSF receptor, the antibody is provided in a format such that the antibody does not kill the cells that express the antigen, e.g., cardiomyocytes that express GM-CSF receptor. Thus, such an antibody may be an antibody fragment that lacks an active Fc region to avoid inducing complement fixation and antibody-dependent cell-mediated cytotoxicity (ADCC).

Antibody Specificity

An antibody for use in the invention binds to GM-CSF or GM-CSF receptor. Any number of techniques can be used to determine antibody binding specificity. See, e.g., Harlow & Lane, Antibodies, A Laboratory Manual (1988) for a description of immunoassay formats and conditions that can be used to determine specific immunoreactivity of an antibody.

An exemplary antibody suitable for use with the present invention is c19/2 or an antibody that has the binding specificity of c19/2. In some embodiments, a monoclonal antibody that competes for binding to the same epitope as c19/2, or that binds the same epitope as c19/2, is used. The ability of a particular antibody to recognize the same epitope as another antibody is typically determined by the ability of the first antibody to competitively inhibit binding of the second antibody to the antigen. Any of a number of competitive binding assays can be used to measure competition between two antibodies to the same antigen. For example, a sandwich ELISA assay can be used for this purpose. This is carried out by using a capture antibody to coat the surface of a well. A subsaturating concentration of tagged-antigen is then added to the capture surface. This protein will be bound to the antibody through a specific antibody:epitope interaction. After washing a second antibody, which has been covalently linked to a detectable moiety (e.g., HRP, with the labeled antibody being defined as the detection antibody) is added to the ELISA. If this antibody recognizes the same epitope as the capture antibody it will be unable to bind to the target protein as that particular epitope will no longer be available for binding. If however this second antibody recognizes a different epitope on the target protein it will be able to bind and this binding can be detected by quantifying the level of activity (and hence antibody bound) using a relevant substrate. The background is defined by using a single antibody as both capture and detection antibody, whereas the maximal signal can be established by capturing with an antigen specific antibody and detecting with an antibody to the tag on the antigen. By using the background and maximal signals as references, antibodies can be assessed in a pair-wise manner to determine epitope specificity.

A first antibody is considered to competitively inhibit binding of a second antibody, if binding of the second antibody to the antigen is reduced by at least 30%, usually at least about 40%, 50%, 60% or 75%, and often by at least about 90%, in the presence of the first antibody using any of the assays described above.

Epitope Mapping

In some embodiments of the invention, an antibody is employed that binds to the same epitope as a known antibody, e.g., c19/2. Method of mapping epitopes are well known in the art. For example, one approach to the localization of functionally active regions of human granulocyte-macrophage colony-stimulating factor (hGM-CSF) is to map the epitopes recognized by neutralizing anti-hGM-CSF monoclonal antibodies. For example, the epitope to which c19/2 (which has the same variable regions as the neutralizing antibody LMM102) binds has been defined using proteolytic fragments obtained by enzymic digestion of bacterially synthesized hGM-CSF (Dempsey, et al., *Hybridoma* 9:545-558, 1990). RP-HPLC fractionation of a tryptic digest resulted in the identification of an immunoreactive "tryptic core" peptide containing 66 amino acids (52% of the protein). Further digestion of this "tryptic core" with *S. aureus* V8 protease produced a unique immunoreactive hGM-CSF product comprising two peptides, residues 86-93 and 112-127, linked by a disulfide bond between residues 88 and 121. The individual peptides, were not recognized by the antibody.

Determining Binding Affinity

In some embodiments, the antibodies suitable for use with the present invention have a high affinity binding for human GM-CSF or GM-CSF receptor. High affinity binding between an antibody and an antigen exists if the dissociation constant ($K_D$) of the antibody is <1 nM, and preferably <100 pM. A variety of methods can be used to determine the binding affinity of an antibody for its target antigen such as surface plasmon resonance assays, saturation assays, or immunoassays such as ELISA or RIA, as are well known to persons of skill in the art. An exemplary method for determining binding affinity is by surface plasmon resonance analysis on a BIAcore™ 2000 instrument (Biacore AB, Freiburg, Germany) using CM5 sensor chips, as described by Krinner et al., (2007) *Mol. Immunol. February;* 44(5):916-25. (Epub 2006 May 11)).

Cell Proliferation Assay for Identifying Neutralizing Antibodies

In some embodiments, the GM-CSF antagonists are neutralizing antibodies to GM-CSF, or its receptor, which bind in a manner that interferes with the binding of GM-CSF. Neutralizing antibodies may be identified using any number of assays that assess GM-CSF function. For example, cell-based assays for GM-CSF receptor signaling, such as assays which determine the rate of proliferation of a GM-CSF-dependent cell line in response to a limiting amount of GM-CSF, are conveniently used. The human TF-1 cell line is suitable for use in such an assay. See, Krinner et al., (2007) *Mol. Immunol.* In some embodiments, the neutralizing antibodies of the invention inhibit GM-CSF-stimulated TF-1 cell proliferation by at least 50% when a GM-CSF concentration is used which stimulates 90% maximal TF-1 cell proliferation. In other embodiments, the neutralizing antibodies inhibit GM-CSF stimulated proliferation by at least 90%. Additional assays suitable for use in identifying neutralizing antibodies suitable for use with the present invention will be well known to persons of skill in the art.

Exemplary Antibodies

Antibodies for use in the invention are known in the art and can be produced using routine techniques. Exemplary antibodies are described. It is understood that the exemplary antibodies can be engineered in accordance with the procedures known in the art and summarized herein to produce antibody fragments, chimeras, and the like by either chemical or recombinant technology.

An exemplary chimeric antibody suitable for use as a GM-CSF antagonist is c19/2. The c/19/2 antibody binds GM-CSF with a monovalent binding affinity of about 10 pM as determined by surface plasmon resonance analysis. SEQ ID NOS:1 and 2 show the heavy and light chain variable region sequence of c19/2 (e.g., WO03/068920). The CDRs, as defined according to Kabat, are:

| CDRH1 | DYNIH | (SEQ ID NO: 22) |
|---|---|---|
| CDRH2 | YIAPYSGGTGYNQEFKN | (SEQ ID NO: 23) |
| CDRH3 | RDRFPYYFDY | (SEQ ID NO: 7) |
| CDRL1 | KASQNVGSNVA | (SEQ ID NO: 24) |
| CDRL2 | SASYRSG | (SEQ ID NO: 25) |
| CDRL3 | QQFNRSPLT. | (SEQ ID NO: 26) |

The CDRs can also be determined using other well known definitions in the art, e.g., Chothia, international ImMunoGeneTics database (IMGT), and AbM.

The GM-CSF epitope recognized by c19/2 has been identified as a product that has two peptides, residues 86-93 and residues 112-127, linked by a disulfide bond between residues 88 and 121. The c19/2 antibody inhibits the GM-CSF-dependent proliferation of a human TF-1 leukemia cell line with an $EC_{50}$ of 30 pM when the cells are stimulated with 0.5 ng/ml GM-CSF. In some embodiments, an anti-GM-CSF antibody for use in the invention retains at least about 50%, or at least about 75%, 80%, 90%, 95%, or 100%, of the antagonist activity of chimeric c19/2.

An antibody for administration, such as c19/2, can be additionally humaneered. For example, the c19/2 antibody can be further engineered to contain human V gene segments.

In some embodiments, a heavy chain of a humaneered anti-GM-CSF antibody for use in the methods of the invention comprises a heavy-chain V-region that comprises the following elements:

1) human heavy-chain V-segment sequences comprising FR1-CDR1-FR2-CDR2-FR3

2) a CDRH3 region comprising the amino acid sequence R(Q/D)RFPY (SEQ ID NO:27)

3) a FR4 contributed by a human germ-line J-gene segment.

Examples of V-segment sequences that support binding to GM-CSF in combination with a CDR3-FR4 segment described above together with a complementary $V_L$ region are shown in FIG. 9. The V-segments can be, e.g., from the human VH1 subclass. In some embodiments, the V-segment is a human $V_H1$ sub-class segment that has a high degree of amino-acid sequence identity, e.g., at least 80%, 85%, or 90% or greater identity, to the germ-line segment VH1 1-02 or VH1 1-03. In some embodiments, the V-segment differs by not more than 15 residues from VH1 1-02 or VH1 1-03 and preferably not more than 7 residues.

The FR4 sequence of the antibodies of the invention of the heavy chains as described here can be provided by a human JH1, JH3, JH4, JH5 or JH6 gene germline segment, or a sequence that has a high degree of amino-acid sequence identity to a human germline JH segment. In some embodiments, the J segment is a human germline JH4 sequence.

The CDRH3 comprising the sequence set forth above can also comprises sequences that are derived from a human J-segment. Typically, the CDRH3-FR4 sequence excluding the BSD differs by not more than 2 amino acids from a human germ-line J-segment. In typical embodiments, the J-segment sequences in CDRH3 are from the same J-segment used for the FR4 sequences. Thus, in some embodiments, the CDRH3-FR4 region comprises the BSD and a complete human JH4 germ-line gene segment. An exemplary combination of CDRH3 and FR4 sequences is shown below (SEQ ID NO:28), in which the BSD is in bold and human germ-line J-segment JH4 residues are underlined:

| CDR3 |
|---|
| R(Q/D)RFPY<u>YFDYWGQGTLVTVSS</u> |

In some embodiments, an antibody for use in the invention has a $V_H$ that comprises a V-segment that has at least 90% identity, or at least 91%, 92% 93%, 94%, 95%, 965, 97%, 98%, 99%, or 100% identity to the germ-line segment VH 1-02 or VH1-03; or to one of the V-segments of the $V_H$ regions shown in FIG. 9, such as a V-segment portion of VH#1, VH#2, VH#3, VH#4, or VH#5. In some embodiments, the V-segment of the $V_H$ region has a CDR1 and/or CDR2 as shown in FIG. 9. For example, an antibody of the invention may have a CDR1 that has the sequence GYYMH (SEQ ID NO:29) or NYYIH (SEQ ID NO:30); or a CDR2 that has the sequence WINPNSGGTNYAQKFQG (SEQ ID NO:31) or WINAG-NGNTKYSQKFQG (SEQ ID NO:32). In further embodiments, an anti-GM-CSF antibody may have both a CDR1 and a CDR2 from one of the $V_H$ region V-segments shown in FIG. 9 and a CDR3 that comprises R(Q/D)RFPY (SEQ ID NO:27), e.g., RDRFPYYFDY (SEQ ID NO:7) or RQRFPYYFDY (SEQ ID NO:6). Thus, in some embodiments, an anti-GM-CSF antibody for use in the invention, may for example, have a CDR3-FR4 that has the sequence R(Q/D)RFPYYFDY-WGQGTLVTVSS (SEQ ID NO:28) and a CDR1 and/or CDR2 as shown in FIG. 9.

In some embodiments, a $V_H$ region of a humaneered antibody for use in the invention has a CDR3 that has a binding specificity determinant R(Q/D)RFPY (SEQ ID NO:27), a CDR2 from a human germline VH1 segment or a CDR1 from a human germline VH1. In some embodiments, both the CDR1 and CDR2 are from human germline VH1 segments.

In some embodiments, a light chain of a humaneered anti-GM-CSF antibody for use in the invention comprises at light-chain V-region that comprises the following elements:
1) human light-chain V-segment sequences comprising FR1-CDR1-FR2-CDR2-FR3
2) a CDRL3 region comprising the sequence FNK or FNR, e.g., QQFNRSPLT (SEQ ID NO:26) or QQFNKSPLT (SEQ ID NO:9).
3) a FR4 contributed by a human germ-line J-gene segment. The $V_L$ region comprises either a Vlambda or a Vkappa V-segment. An example of a Vkappa sequence that supports binding in combination with a complementary $V_H$-region is provided in FIG. 9.

The $V_L$ region CDR3 sequence described above can comprise a J-segment derived sequence. In typical embodiments, the 3-segment sequences in CDRL3 are from the same J-segment used for FR4. Thus, the sequence in some embodiments may differ by not more than 2 amino acids from human kappa germ-line V-segment and J-segment sequences. In some embodiments, the CDRL3-FR4 region comprises the BSD and the complete human JK4 germline gene segment. Exemplary CDRL3-FR4 combinations for kappa chains are shown below (SEQ ID NOS:33 and 34) in which the minimal essential binding specificity determinant is shown in bold and JK4 sequences are underlined:

CDR3
QQFNRS<u>PLTFGGGTKVEIK</u>

QQFNKS<u>PLTFGGGTKVEIK</u>

The Vkappa segments are typically of the VKIII sub-class. In some embodiments, the segments have at least 80% sequence identity to a human germline VKIII subclass, e.g., at least 80% identity to the human germ-line VKIIIA27 sequence. In some embodiments, the Vkappa segment may differ by not more than 18 residues from VKIIIA27. In other embodiments, the $V_L$ region V-segment of an antibody of the invention has at least 85% identity, or at least 90%, 91%, 92%, 93%, 94%, 95%, 96%, 97%, 98%, 99%, or 100% identity to the human kappa V-segment sequence of a $V_L$ region shown in FIG. 9, for example, the V-segment sequence of VK#1, VK#2, VK#3, or VK#4. In some embodiments, the V-segment of the $V_L$ region has a CDR1 and/or CDR2 as shown in FIG. 9. For example, an antibody of the invention may have a CDR1 sequence of RASQSVGTNVA (SEQ ID NO:35) or RASQSIGSNLA (SEQ ID NO:36); or a CDR2 sequence STSSRAT (SEQ ID NO:37). In particular embodiments, an anti-GM-CSF antibody of the invention may have a CDR1 and a CDR2 in a combination as shown in one of the V-segments of the $V_L$ regions set forth in FIG. 9 and a CDR3 sequence that comprises FNK or FNR, e.g., the CDR3 may be QQFNKSPLT (SEQ ID NO:9) or QQFNRSPLT (SEQ ID NO:26). In some embodiments, such a GM-CSF antibody may comprise an FR4 region that is FGGGTKVEIK (SEQ ID NO:38). Thus, an anti-GM-CSF antibody of the invention, can comprise, e.g., both the CDR1 and CDR2 from one of the $V_L$ regions shown in FIG. 9 and a CDR3-FR4 region that is FGGGTKVEIK (SEQ ID NO:38).

An antibody for use in the invention may thus comprise any of the $V_H$ regions VH#1, VH#2, VH#3, VH#4, or VH#5 as shown in FIG. 9. In some embodiment, an antibody of the invention may comprise any of the $V_L$ regions VK#1, VK#2, VK#3, or VK#4 as shown in FIG. 9. In some embodiments, the antibody has a $V_H$ region VH#1, VH#2, VH#3, VH#4, or VH#5 as shown in FIG. 9; and a VL regions VK#1, VK#2, VK#3, or VK#4 as shown in FIG. 9.

Another exemplary neutralizing anti-GM-CSF antibody is the E10 antibody described in Li et al., (2006) *PNAS* 103(10): 3557-3562. E10 is an IgG class antibody that has an 870 pM binding affinity for GM-CSF. The antibody is specific for binding to human GM-CSF as shown in an ELISA assay, and shows strong neutralizing activity as assessed with a TF1 cell proliferation assay.

An additional exemplary neutralizing anti-GM-CSF antibody is the MT203 antibody described by Krinner et al., (*Mol. Immunol.* 44:916-25, 2007; Epub 2006 May 112006). MT203 is an IgG1 class antibody that binds GM-CSF with picomolar affinity. The antibody shows potent inhibitory activity as assessed by TF-1 cell proliferation assay and its ability to block IL-8 production in U937 cells. Additional GM-CSF antibodies are described, e.g., by Steidl et al. in WO2006122797. MOR04357 (Steidl et al., *Molec. Immunol.,* 2008 November; 46(1):135-44. Epub 2008 Aug. 21.) may also be used in the methods of the invention.

Additional antibodies suitable for use with the present invention will be known to persons of skill in the art.

GM-CSF antagonists that are anti-GM-CSF receptor antibodies can also be employed in the invention. Such GM-CSF antagonists include antibodies to the GM-CSF receptor alpha chain or beta chain. In some embodiments, the GM-CSF receptor antibody for use in the invention is to the alpha chain. An anti-GM-CSF receptor antibody employed in the invention can be in any antibody format as explained above, e.g., intact, chimeric, monoclonal, polyclonal, antibody fragment, humanized, humaneered, and the like. Examples of anti-GM-CSF receptor antibodies, e.g., neutralizing, high-affinity antibodies, suitable for use in the invention are known (see, e.g., U.S. Pat. No. 5,747,032 and Nicola et al., *Blood* 82: 1724, 1993).

Non-Antibody GM-CSF Antagonists

Other proteins which may interfere with the productive interaction of GM-CSF with its receptor include mutant GM-CSF proteins and secreted proteins comprising at least part of the extracellular portion of one or both of the GM-CSF receptor chains that bind to GM-CSF and compete with binding to cell-surface receptor. For example, a soluble GM-CSFR antagonist can be prepared by fusing the coding region of the sGM-CSFRalpha with the CH2-CH3 regions of murine IgG2a. An exemplary soluble GM-CSF receptor is described by Raines et al. (1991) *Proc. Natl. Acad. Sci. USA* 88: 8203. Examples of GM-CSFRalpha-Fc fusion proteins are provided, e.g., in Brown et al., *Blood* 85:1488, 1995; Monfardini et al., *J. Biol. Chem.* 273:7657-7667, 1998; and Sayani et al., *Blood* 95:461-469, 2000. In some embodiments, the Fc component of such a fusion can be engineered to modulate binding, e.g., to increase binding, to the Fc receptor.

Other GM-CSF antagonist include GM-CSF mutants. For example, GM-CSF having a mutation of amino acid residue 21 of GM-CSF to Arginine or Lysine (E21R or E221K) described by Hercus et al., *Proc. Natl. Acad. Sci. USA* 91:5838, 1994 has been shown to have in vivo activity in preventing dissemination of GM-CSF-dependent leukemia cells in mouse xenograft models (Iversen et al. *Blood* 90:4910, 1997). As appreciated by one of skill in the art, such antagonists can include conservatively modified variants of GM-CSF that have substitutions, such as the substitution noted at amino acid residue 21, or GM-CSF variants that have, e.g., amino acid analogs to prolong half-life.

Other GM-CSF peptide inhibitors are also known, e.g., cyclic peptides, e.g., Monfardini, et al., *J. Biol. Chem.* 271: 1966-1971, 1996.

In other embodiments, the GM-CSF antagonist is an "antibody mimetic" that targets and binds to the antigen in a manner similar to antibodies. Certain of these "antibody mimics" use non-immunoglobulin protein scaffolds as alternative protein frameworks for the variable regions of antibodies. For example, Ku et al. (*Proc. Natl. Acad. Sci. U.S.A.* 92(14):6552-6556 (1995)) discloses an alternative to antibodies based on cytochrome b562 in which two of the loops of cytochrome b562 were randomized and selected for binding against bovine serum albumin. The individual mutants were found to bind selectively with BSA similarly with anti-BSA antibodies.

U.S. Pat. Nos. 6,818,418 and 7,115,396 disclose an antibody mimic featuring a fibronectin or fibronectin-like protein scaffold and at least one variable loop. Known as Adnectins, these fibronectin-based antibody mimics exhibit many of the same characteristics of natural or engineered antibodies, including high affinity and specificity for any targeted ligand. The structure of these fibronectin-based antibody mimics is similar to the structure of the variable region of the IgG heavy chain. Therefore, these mimics display antigen binding properties similar in nature and affinity to those of native antibodies. Further, these fibronectin-based antibody mimics exhibit certain benefits over antibodies and antibody fragments. For example, these antibody mimics do not rely on disulfide bonds for native fold stability, and are, therefore, stable under conditions which would normally break down antibodies. In addition, since the structure of these fibronectin-based antibody mimics is similar to that of the IgG heavy chain, the process for loop randomization and shuffling may be employed in vitro that is similar to the process of affinity maturation of antibodies in vivo.

Beste et al. (*Proc. Natl. Acad. Sci. U.S.A.* 96(5):1898-1903 (1999)) disclose an antibody mimic based on a lipocalin scaffold (Anticalin®). Lipocalins are composed of a β-barrel with four hypervariable loops at the terminus of the protein. The loops were subjected to random mutagenesis and selected for binding with, for example, fluorescein. Three variants exhibited specific binding with fluorescein, with one variant showing binding similar to that of an anti-fluorescein antibody. Further analysis revealed that all of the randomized positions are variable, indicating that Anticalin® would be suitable to be used as an alternative to antibodies. Thus, Anticalins® are small, single chain peptides, typically between 160 and 180 residues, which provides several advantages over antibodies, including decreased cost of production, increased stability in storage and decreased immunological reaction.

U.S. Pat. No. 5,770,380 discloses a synthetic antibody mimetic using the rigid, non-peptide organic scaffold of calixarene, attached with multiple variable peptide loops used as binding sites. The peptide loops all project from the same side geometrically from the calixarene, with respect to each other. Because of this geometric confirmation, all of the loops are available for binding, increasing the binding affinity to a ligand. However, in comparison to other antibody mimics, the calixarene-based antibody mimic does not consist exclusively of a peptide, and therefore it is less vulnerable to attack by protease enzymes. Neither does the scaffold consist purely of a peptide, DNA or RNA, meaning this antibody mimic is relatively stable in extreme environmental conditions and has a long life span. Further, since the calixarene-based antibody mimic is relatively small, it is less likely to produce an immunogenic response.

Murali et al. (*Cell Mol Biol* 49(2):209-216 (2003)) describe a methodology for reducing antibodies into smaller peptidomimetics, they term "antibody like binding peptidomimetics" (ABiP) which may also be useful as an alternative to antibodies.

WO 00/60070 discloses a polypeptide chain having CTL4A-like β-sandwich architecture. The peptide scaffold has from 6 to 9β-strands, wherein two or more of the polypeptide β-loops constitute binding domains for other molecules, such as antigen binding fragments. The basic design of the scaffold is of human origin, thus reducing the risk of inducing an immune response. The β-sandwich scaffold may have improved stability and pharmacokinetic properties in vivo when compared to standard antibodies as the molecule contains a second, non-immunoglobulin disulphide bridge. As antigen binding domains can be located at opposite ends of a single peptide chain, the β-sandwich also facilitates design of bispecific monomeric molecules.

In addition to non-immunoglobulin protein frameworks, antibody properties have also been mimicked in compounds comprising RNA molecules and unnatural oligomers (e.g., protease inhibitors, benzodiazepines, purine derivatives and beta-turn mimics). Accordingly, non-antibody GM-CSF antagonists can also include such compounds.

III. Therapeutic Administration

The methods of the invention comprise administering a GM-CSF antagonist (e.g., an anti-GM-CSF antibody) as a pharmaceutical composition to a patient with heart failure, or at risk for developing heart failure due to an ischemic episode such as a heart attack, or a patient that has a cardiomyopathy, e.g., dilated cardiomyopathy, in a therapeutically effective amount using a dosing regimen suitable for treatment of the disease. The composition can be formulated for use in a variety of drug delivery systems. One or more physiologically acceptable excipients or carriers can also be included in the compositions for proper formulation. Suitable formulations for use in the present invention are found in *Remington: The Science and Practice of Pharmacy,* 21 st Edition, Philadelphia, Pa. Lippincott Williams & Wilkins, 2005. For a brief review of methods for drug delivery, see, Langer, *Science* 249: 1527-1533 (1990).

The GM-CSF antagonist for use in the methods of the invention is provided in a solution suitable for injection into the patient such as a sterile isotonic aqueous solution for injection. The GM-CSF antagonist is dissolved or suspended at a suitable concentration in an acceptable carrier. In some embodiments the carrier is aqueous, e.g., water, saline, phosphate buffered saline, and the like. The compositions may contain auxillary pharmaceutical substances as required to approximate physiological conditions, such as pH adjusting and buffering agents, tonicity adjusting agents, and the like.

The GM-CSF antagonist pharmaceutical compositions of the invention are administered to a patient with heart failure and/or a patient that has experienced an ischemic episode or has a cariomyopathy, in an amount sufficient to at least partially arrest symptoms of heart failure and its complications; or at least partially slow or arrest the onset of symptoms of heart failure. An amount adequate to accomplish this is defined as a "therapeutically effective dose." A therapeutically effective dose is determined by monitoring a patient's response to therapy. A typical benchmark is left ventricular ejection fraction. Amounts effective for this use will depend upon the severity of the disease and the general state of the patient's health, including other factors such as age, weight, gender, administration route, etc. Single or multiple administrations of the antagonist may be administered depending on the dosage and frequency as required and tolerated by the patient. In any event, the methods provide a sufficient quantity of GM-CSF antagonist to effectively treat the patient.

In some embodiments, the GM-CSF antagonist is administered after a patient has suffered from an ischemic episode, such as an acute myocardial infarction. For example, the GM-CSF antagonist, i.e., an anti-GM-CSF antibody, may be administered within two weeks, often within one week, and in some embodiments within about 48 hours or about 24 hours or less, of the heart attack. A patient may undergo subsequent additional treatments with the GM-CSF antagonist.

In some embodiments, the GM-CSF antagonist is administered to a patient that has been diagnosed with heart failure using conventional diagnostic guidelines, e.g., such as those described herein. Such a patient often may have had a heart attack.

In some embodiments of the invention, the GM-CSF antagonist used to treat a patient that has heart failure or is at risk for heart failure due to an ischemic episode, is provided in combination another therapeutic agent, such as an Angiotensin-Converting Enzyme (ACE) inhibitor, an angiotensin receptor blocker, a beta blocker, a diuretic, a positive inotrope, or a vasodilator. Accordingly, in some embodiments, the GM-CSF antagonist, e.g., an anti-GM-CSF antibody, is administered to a patient who is also being treated with an ACE inhibitor such as a sulfhydryl-containing ACE inhibitor, e.g., captopril or zofenopril; a dicarboxylate-containing ACE inhibitor, e.g., enalapril, ramipril, quinapril, perindopril, lisinopril, or benazepril; and a phosphonate-containing ACE inhibitor such as fosinopril. In other embodiments, the GM-CSF antagonist, e.g., an anti-GM-CSF antibody, is administered to a patient that is being treated with an angiotensin receptor blocker such as candesartan, losartan, irbesartan, valsartan, olmesartan, telmisartan, or eprosartan; or a beta blocker such as bisoprolol, carvedilol, and metoprolol. In some embodiments, a GM-CSF antagonist, e.g., an anti-GM-CSF antibody is administered to a patient who is being treated with a diruretic, such as a loop diuretics (e.g., furosemide, bumetanide); a thiazide diuretics (e.g., hydrochlorothiazide, chlorthalidone, chlorthiazide); a potassium-sparing diuretic (e.g., amiloride); and/or spironolactone or eplerenone. As understood in the art, a patient may be treated with various combinations of such agents in addition to receiving a GM-CSF antagonist.

A patient may undergo treatment with the GM-CSF antagonist and one or more additional another therapeutic agents either concomitantly or sequentially. In some embodiments, a patient may initially be treated with an agent and then receive treatment with the GM-CSF antagonist after treatment with the other therapeutic agent has been discontinued, e.g., due to deleterious side effects of the therapeutic agent. In some embodiments, a lower dose, and/or less frequent dosages, of the additional therapeutic agent, may be used when the patient also undergoes treatment with a GM-CSF antagonist, e.g., a GM-CSF antibody, in comparison to the amount of therapeutic agent typically administered to a patient. As understood in the art, the dosages and frequency of administration of the GM-CSF antagonist may also be adjusted when used in combination with another therapeutic agent for the treatment of heart failure.

A. Administration

In some embodiments, the GM-CSF antagonist is an antibody that is administered by injection or infusion through any suitable route including but not limited to intravenous, subcutaneous, intramuscular or intraperitoneal routes.

In an exemplary embodiment, the antibody is stored at 10 mg/ml in sterile isotonic aqueous saline solution for injection at 4° C. and is diluted in either 100 ml or 200 ml 0.9% sodium chloride for injection prior to administration to the patient. The antibody is administered by intravenous infusion over the course of 1 hour at a dose of between 0.2 and 10 mg/kg. In other embodiments, the antibody is administered by intravenous infusion over a period of between 15 minutes and 2 hours. In still other embodiments, the administration procedure is via sub-cutaneous bolus injection.

B. Dosing

The dose of antagonist is chosen in order to provide effective therapy for the patient and is in the range of less than 0.1 mg/kg body weight to 25 mg/kg body weight or in the range 1 mg-2 g per patient. Preferably the dose is in the range 1-10 mg/kg or approximately 50 mg-1000 mg/patient. The dose may be repeated at an appropriate frequency which may be in the range once per day to once every three months, depending on the pharmacokinetics of the antagonists (e.g. half-life of the antibody in the circulation) and the pharmacodynamic response (e.g. the duration of the therapeutic effect of the antibody). In some embodiments where the antagonist is an antibody or modified antibody fragment, the in vivo half-life of between about 7 and about 25 days and antibody dosing is repeated between once per week and once every 3 months. In other embodiments, the antibody is administered approximately once per month.

EXAMPLES

Example 1

A GM-CSF Antibodies Decreases Cardiac Re-Modeling and Improves Left Ventricular Function This study was designed to determine if blocking the effects of GM-CSF alters left ventricular (LV) remodeling and hemodynamics in rats with acute myocardial infarction (MI).

Figure 2:
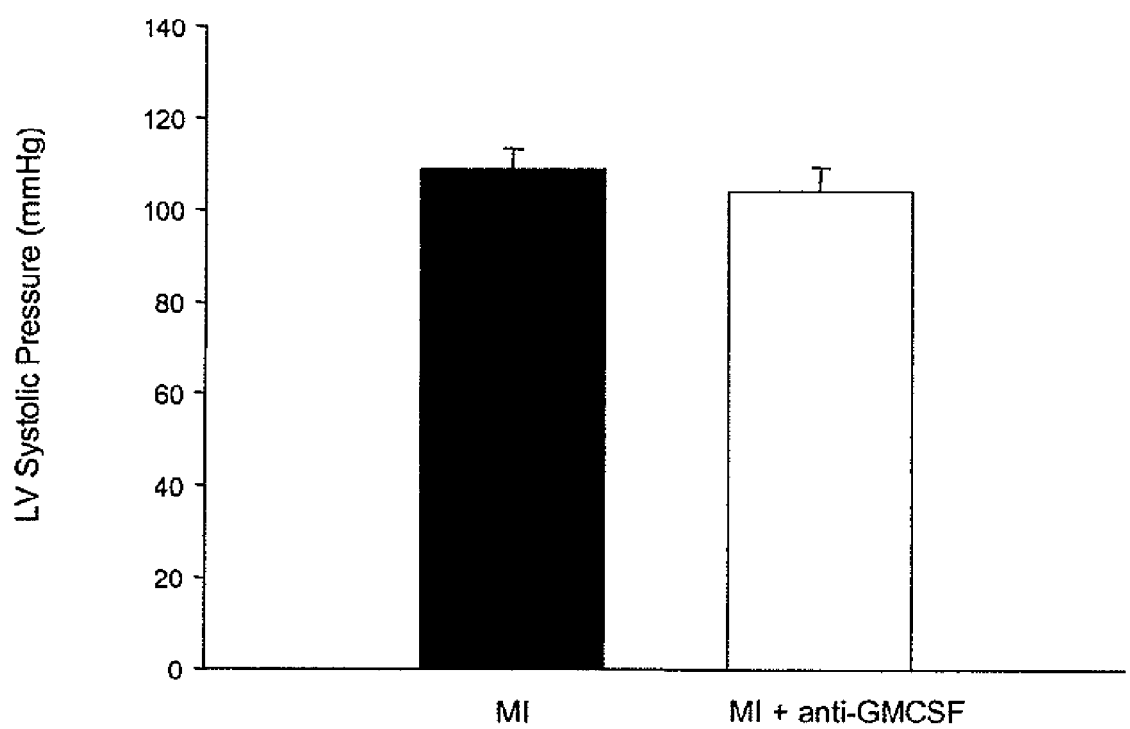
Figure 3:
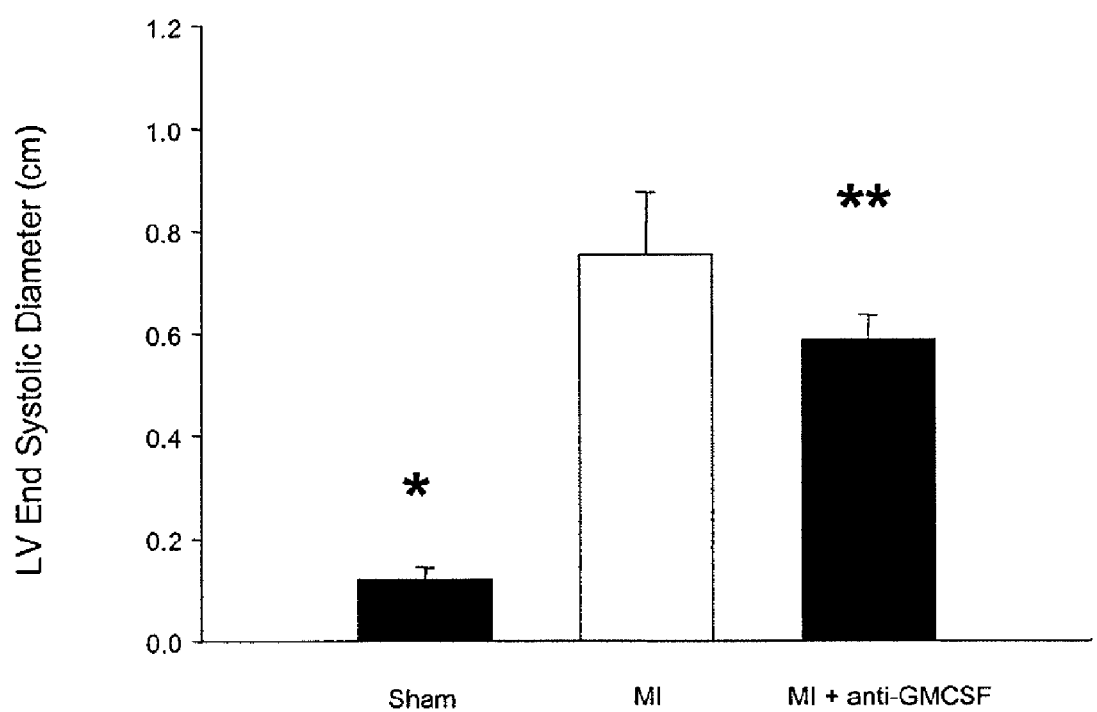
FIG. 3 provides data showing the effects of anti-GM-CSF antibody on global left ventricular (LV) end systolic diameter in infarcted rats. The graph shows the left ventricular end systolic diameter (cm) for sham, MI and MI+anti-GMCSF. Data are mean±SE. Sham (N=6), MI (N=10), MI+anti-GM-CSF (N=10)* P<0.05 vs MI+anti-GM-CSF;  P <0.05 vs MI FIG. 4** provides data showing the effect of anti-GM-CSF antibody on left ventricular (LV) end diastolic diameter in infarcted rats. The graph shows the LV end diastolic diameter (cm) in sham, MI and MI+anti-GMCSF treated animals. Data are mean±SE. *P<0.05 versus MI and mI+anti-GM-CSF; Sham (N=4), MI (N=12), MI+anti-GM-CSF (N=10)

Acute MI was created by ligating the left coronary artery of rats; treatment with anti-rat GM-CSF antibody (Mab518 R&D Systems Inc; 5 mg/kg) was initiated 24 h prior to coronary ligation. Antibody Mab 518 is a GM-CSF neutralizing antibody. 0.8 µg/ml Mab 518 inhibits greater than 50% activity of 0.5 ng/ml rat GM-CSF in a mouse DA-3 cell proliferation assay. Antibody was dosed by intraperitoneal (i.p) administration three times per week for 3 weeks. Closed-chest echocardiography and solid-state micromanometers were used to measure outcome variables 3 weeks after ligation. N=6-10 in each group. FIG. 1 shows the global left ventricular function among treated groups. FIGS. 2 and 3 show the left ventricular systolic pressure and left ventricular end systolic diameter, respectively, in treatment groups.

Figure 4:
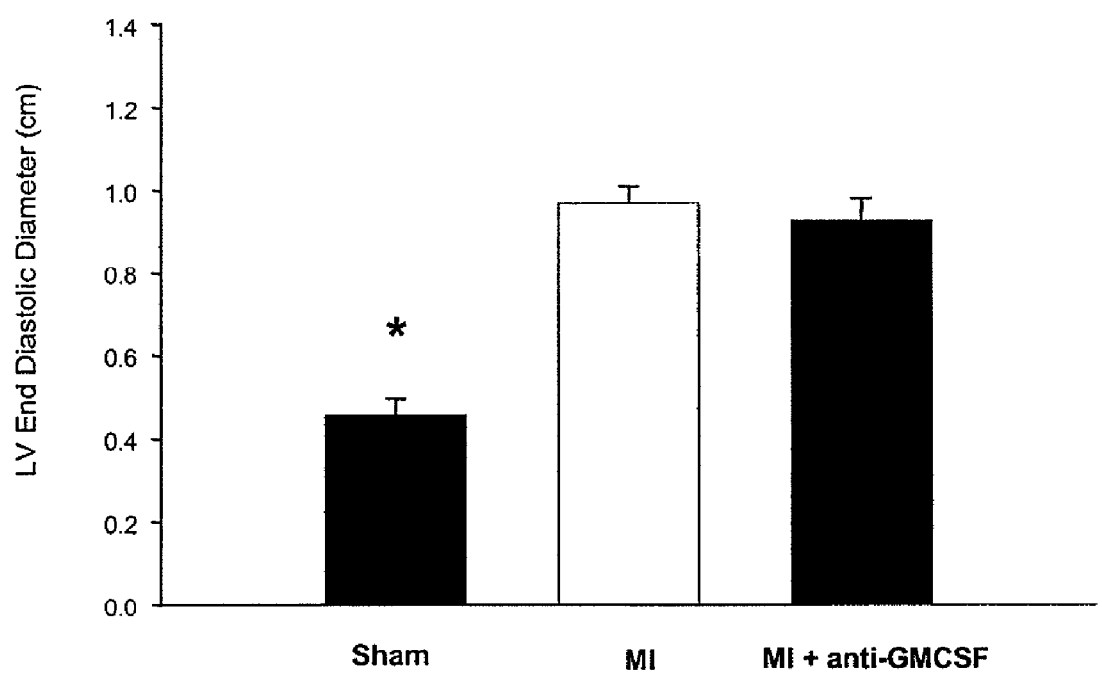
Figure 5:
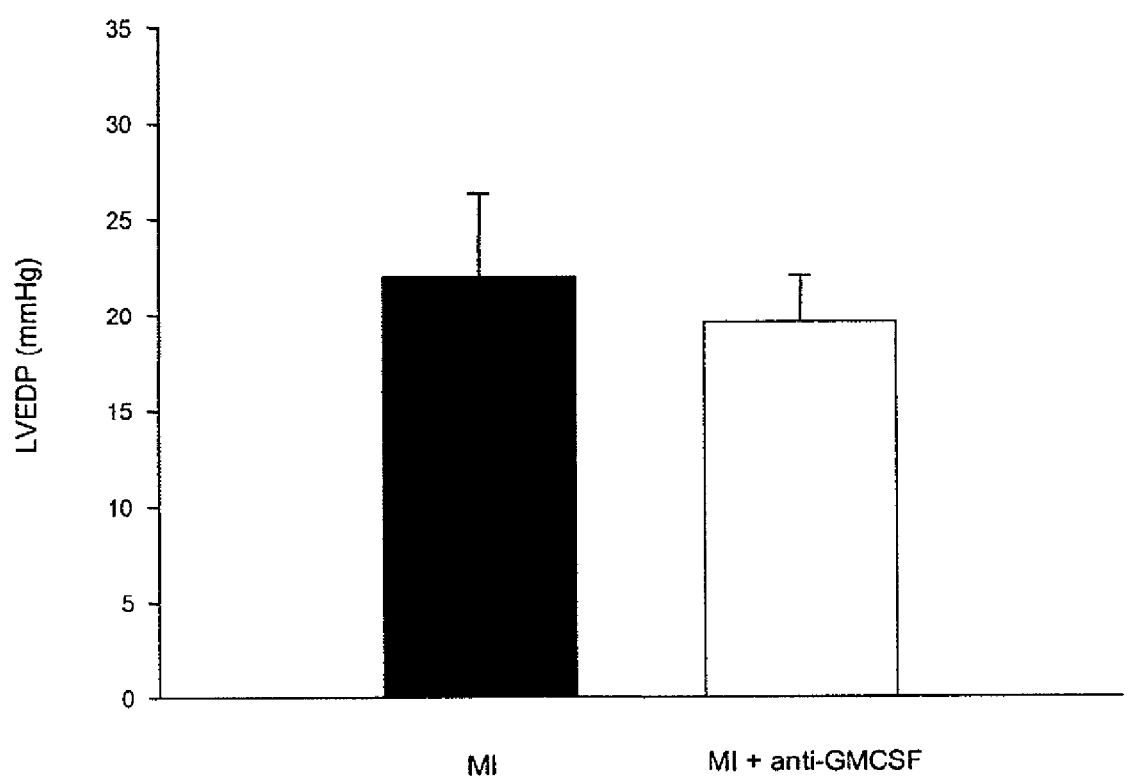
FIG. 5 provides data showing the effect of anti-GM-CSF antibody on left ventricular end diastolic pressure (LVEDP) in infarcted rats. The graph shows LVEDP (mmHg) in MI and MI+anti-GM-CSF treated animals. N=3 for MI; N=4 for MI+anti-GM-CSF FIG. 6 provides data showing the effects of an anti-GM-CSF antibody on Tau in infarcted rats. The graph shows Tau (left ventricular relaxation time constant) for animals in MI and MI+anti-GM-CSF treatment groups.
Figure 6:
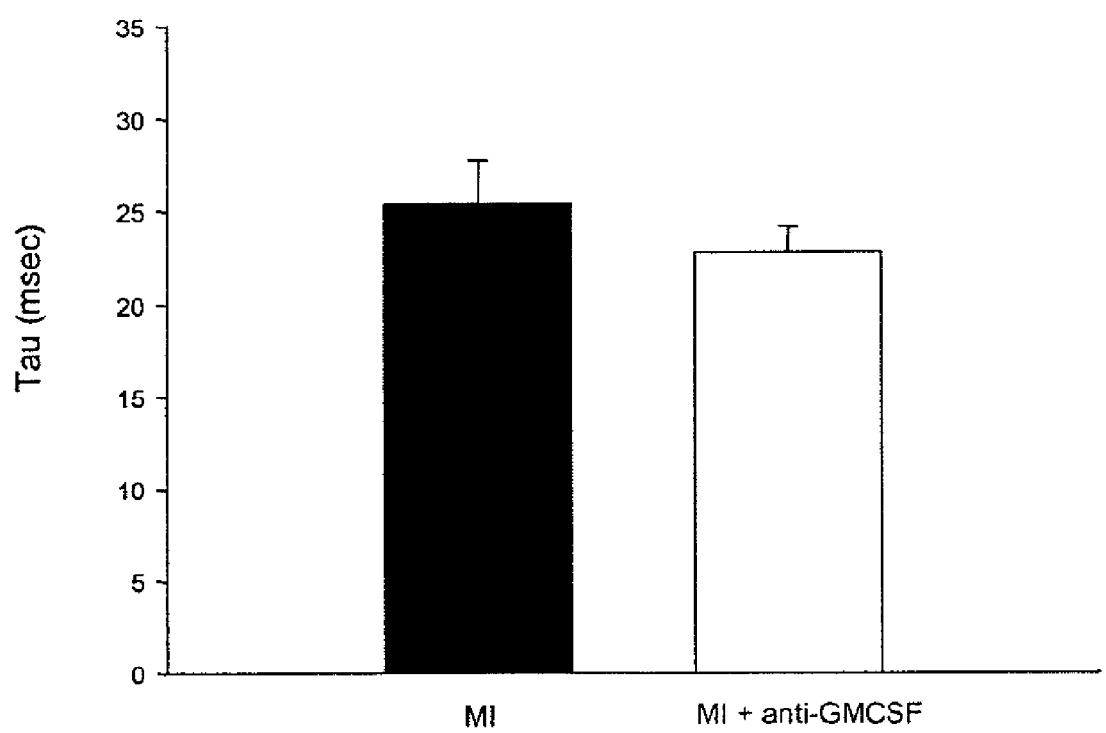

In these experiments, the GM-CSF antibody significantly increased ($P<0.05$) left ventricular ejection fraction (37±3 vs 47±5%) (FIG. 1) and decreased ($P<0.05$) left ventricular end-systolic diameter (0.75±0.12 vs. 0.59+0.05 cm) (FIG. 3) with no changes in left ventricular systolic pressure (109+4 vs 104+5 mmHg) (FIG. 2), left ventricular-end diastolic diameter (0.96+0.04 vs. 0.92+0.05 cm) (FIG. 4), left ventricular-end diastolic pressure (22+4 vs 21+2 mmHg) (FIG. 5), or Tau (25.4+2.4 vs. 22.7±1.4 msec) (FIG. 6).

These studies demonstrate that treatment with antibody against GM-CSF improves left ventricular ejection fraction and partially reverses left ventricular re-modeling (e.g., decreases LV end-systolic diameter).

At the end of the study, hearts were excised and left ventricles were processed for immunohistochemical analysis. Immunohistochemical analysis was carried out using antibodies to rat CD68 (ED1; Serotec) and Gs-1 lectin according to the manufacturer's instructions. Milligan's trichrome staining was used to identify areas of infarction.

Figure 7:
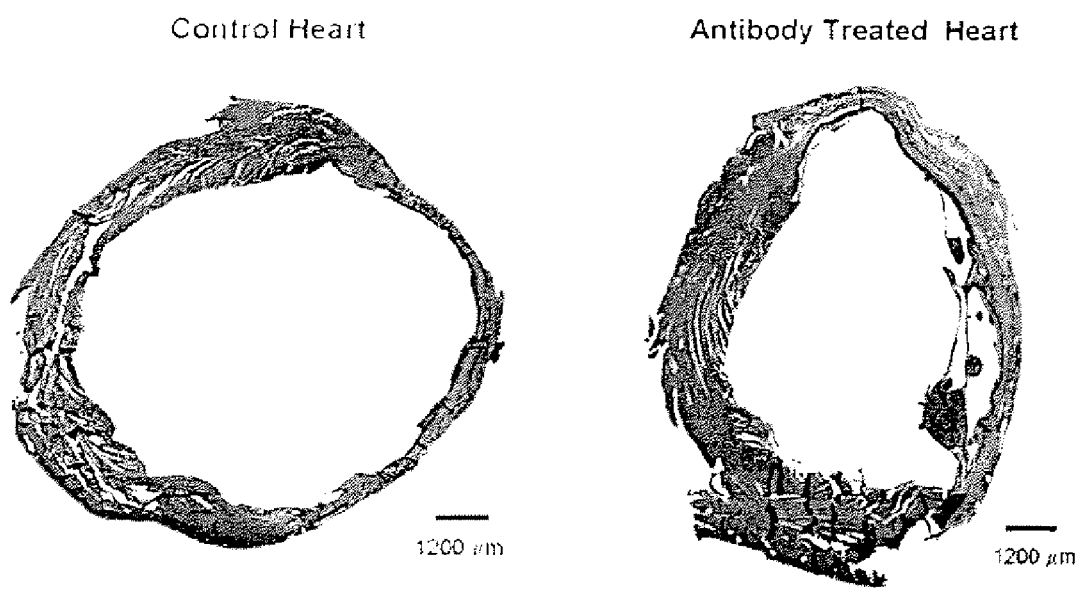
FIG. 7 provides data showing the results of Milligan's trichrome staining of left ventricle cross sections of control and GM-CSF antibody-treated hearts 3 weeks after coronary-artery ligation. Infarcted regions of the heart are clearly visible due to the thinning of the myocardial wall.

Sections of the left ventricle stained with Milligan's trichrome stain are shown in FIG. 7. Significant infarction is shown by the area of thinned myocardium in vehicle-treated animals 3 weeks after legation of the coronary artery. The effect of anti-GM-CSF antibody treatment was detected by determining the thickness of the myocardial wall in the infarcted region and by staining for collagen and muscle fibers. Measurements of myocardial wall thickness in hearts from multiple animals did not identify significant differences between control and treated groups.

CD68-positive activated macrophages were quantified in infarcted regions of the hearts from 5 animals selected to show major infarcts (significant areas of thinned myocardium). Three distinct areas of the infarct zone were chosen for morphometric analysis in each heart and the mean number of CD68-positive cells scored. Blood vessels were analyzed using Gs-1 lectin in a similar manner. Microvessel density was scored for infracted areas of 3 representative hearts.

Figure 8:
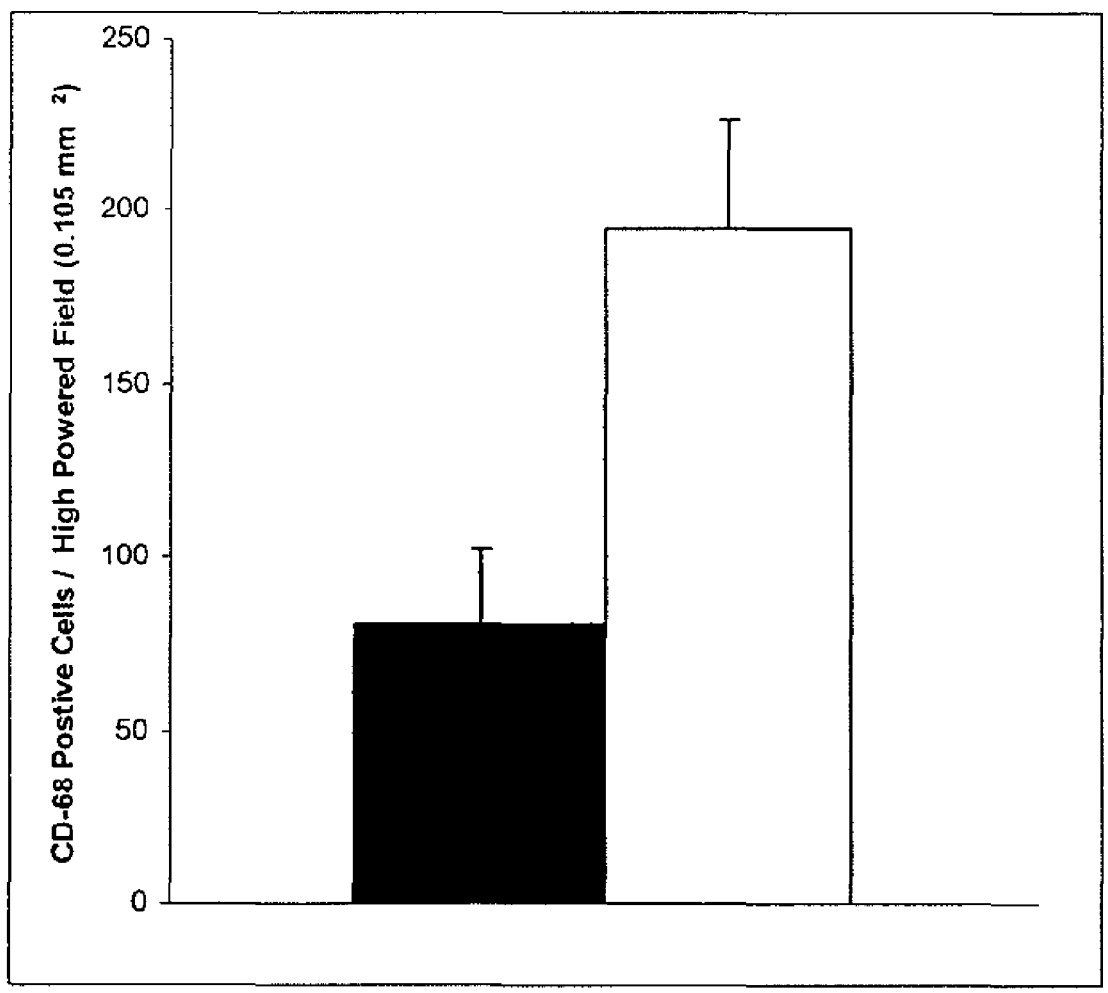
FIG. 8 shows the number of CD68-positive macrophages in infarcted heart tissue of rats treated with anti-GM-CSF antibody (black bar) or vehicle-treated animals (white bar). Mean number of CD68-positive cells per high-powered micrograph and standard error are shown (n=5 rats). * difference in means is statistically significant (P=0.0002 determined by two-tailed t-test).

The effect of anti-GM-CSF antibody treatment on the number of infiltrating CD68-positive macrophages into the infarcted areas of the heart is shown in FIG. 8. Infiltration of large numbers of CD68-positive macrophages was observed in sections of the heart in control animals 3 weeks after ligation of the coronary artery, as has been described previously in the rat coronary artery ligation model (Naito et al, *Immunol* 181: 5691-5701, 2008). Treatment with Mab518 led to a marked reduction in the number of infiltrating macrophages compared with hearts from vehicle-treated animals from a mean of 195 cells/0.105 mm$^2$ field in control hearts to a mean of 81 cells/0.105 mm$^2$ in hearts from anti-GM-CSF treated animals. No significant differences in microvessel density were observed in infarcted myocardium from treated or control animals.

Not to be bound by theory, these data are consistent with a model in which GM-CSF neutralization post myocardial infarction acts inhibits re-modeling by reducing the infiltration and activation of tissue macrophages in infarcted tissues.

Example 2

Exemplary Humaneered Antibodies to GM-CSF

A panel of humaneered Fab' molecules with the specificity of c19/2 were generated from epitope-focused human V-segment libraries as described in US patent application 20060134098.

Fab' fragments were expressed from *E. coli*. Cells were grown in 2×YT medium to an OD600 of 0.6. Expression was induced using IPTG for 3 hours at 33° C. Assembled Fab' was obtained from periplasmic fractions and purified by affinity chromatography using Streptococcal Protein G (HiTrap Protein G HP columns; GE Healthcare) according to standard methods. Fab's were eluted in pH 2.0 buffer, immediately adjusted to pH 7.0 and dialyzed against PBS pH7.4.

Binding kinetics were analyzed by Biacore 3000 surface plasmon resonance (SPR). Recombinant human GM-CSF antigen was biotinylated and immobilized on a streptavidin CM5 sensor chip. Fab samples were diluted to a starting concentration of 3 nM and run in a 3 fold dilution series. Assays were run in 10 mM HEPES, 150 mM NaCl, 0.1 mg/mL BSA and 0.005% p20 at pH 7.4 and 37° C. Each concentration was tested twice. Fab' binding assays were run on two antigen density surfaces providing duplicate data sets. The mean affinity ($K_D$) for each of 6 humaneered anti-GM-CSF Fab clones, calculated using a 1:1 Langmuir binding model, is shown in Table 1.

Fabs were tested for GM-CSF neutralization using a TF-1 cell proliferation assay. GM-CSF-dependent proliferation of human TF-1 cells was measured after incubation for 4 days with 0.5 ng/ml GM-CSF using a MTS assay (Cell titer 96, Promega) to determine viable cells. All Fabs inhibited cell proliferation in this assay indicating that these are neutralizing antibodies. There is a good correlation between relative affinities of the anti-GM-CSF Fabs and $EC_{50}$ in the cell-based assay. Anti-GM-CSF antibodies with monovalent affinities in the range 18 pM-104 pM demonstrate effective neutralization of GM-CSF in the cell-based assay.

TABLE 1

Affinity of anti-GM-CSF Fabs determined by surface plasmon resonance analysis in comparison with activity ($EC_{50}$) in a GM-CSF dependent TF-1 cell proliferation assay

| Fab | Monovalent binding affinity determined by SPR (pM) | $EC_{50}$ (pM) in TF-1 cell proliferation assay |
| --- | --- | --- |
| 94 | 18 | 165 |
| 104 | 19 | 239 |
| 77 | 29 | 404 |
| 92 | 58 | 539 |
| 42 | 104 | 3200 |
| 44 | 81 | 7000 |

Example 3

Clinical Protocol for Delivery of Anti-GM-CSF Antibody

An anti-GM-CSF antibody is stored at 10 mg/ml in sterile isotonic aqueous saline solution for injection at 4° C. and is diluted in either 100 ml or 200 ml 0.9% sodium chloride for injection prior to administration to a patient suffering from acute myocardial infarction. Additional standard pharmaceutically acceptable excipients (see, e.g., *Remington: The Science and Practice of Pharmacy*, supra) may also be included. The antibody is administered to the patient by intravenous infusion over the course of 1 hour at a dose of between 0.2 and 10 mg/kg.

The above examples are provided by way of illustration only and not by way of limitation. Those of skill in the art will readily recognize a variety of noncritical parameters that could be changed or modified to yield essentially similar results.

All publications, patent applications, accession numbers, and other references cited in this specification are herein incorporated by reference as if each individual publication or patent application were specifically and individually indicated to be incorporated by reference.

Examples of Anti-GM-CSF Variable Region Sequences

SEQ ID NO 1: amino acid sequence for murine 19/2 heavy chain variable region
Met Glu Leu Ile Met Leu Phe Leu Leu Ser Gly Thr
Ala Gly Val His Ser Glu Val Gln Leu Gln Gln Ser
Gly Pro Glu Leu Val Lys Pro Gly Ala Ser Val Lys
Ile Ser Cys Lys Ala Ser Gly Tyr Thr Phe Thr Asp
Tyr Asn Ile His Trp Val Lys Gln Ser His Gly Lys
Ser Leu Asp Trp Ile Gly Tyr Ile Ala Pro Tyr Ser
Gly Gly Thr Gly Tyr Asn Gln Glu Phe Lys Asn Arg
Ala Thr Leu Thr Val Asp Lys Ser Ser Ser Thr Ala
Tyr Met Glu Leu Arg Ser Leu Thr Ser Asp Asp Ser
Ala Val Tyr Tyr Cys Ala Arg Arg Asp Arg Phe Pro
Tyr Tyr Phe Asp Tyr Trp Gly Gln Gly Thr Thr Leu
Arg Val Ser Ser Val Ser Gly Ser SEQ ID NO 2: amino acid sequence for murine 19/2 light chain variable region
Met Gly Phe Lys Met Glu Ser Gln Ile Gln Val Phe
Val Tyr Met Leu Leu Trp Leu Ser Gly Val Asp Gly
Asp Ile Val Met Ile Gln Ser Gln Lys Phe Val Ser
Thr Ser Val Gly Asp Arg Val Asn Ile Thr Cys Lys
Ala Ser Gln Asn Val Gly Ser Asn Val Ala Trp Leu
Gln Gln Lys Pro Gly Gln Ser Pro Lys Thr Leu Ile
Tyr Ser Ala Ser Tyr Arg Ser Gly Arg Val Pro Asp
Arg Phe Thr Gly Ser Gly Ser Gly Thr Asp Phe Ile
Leu Thr Ile Thr Thr Val Gln Ser Glu Asp Leu Ala
Glu Tyr Phe Cys Gln Gln Phe Asn Arg Ser Pro Leu
Thr Phe Gly Ser Gly Thr Lys Leu Glu Leu Lys Arg
Ala Asp Ala Ala Pro Thr Val Ser Ile Phe Pro Pro
Ser Ser Lys Gly Glu Phe

---

What is claimed is:

1. A method for treating a patient that has heart failure, the method comprising administering a therapeutically effective amount of a granulocyte macrophage colony stimulating factor (GM-CSF) antagonist to the patient, wherein the antagonist is an anti-GM-CSF antibody.

2. The method of claim 1, wherein the patient has a left ventricular ejection fraction of 40% or less.

3. The method of claim 1, wherein the patient has Class II, Class III, or Class IV heart failure as determined with reference to the New York Heart Association classification.

4. The method of claim 1, wherein the patient is being treated with an angiotensin-converting enzyme (ACE) inhibitor.

5. The method of claim 1, wherein the anti-GM-CSF antibody is a monoclonal antibody.

6. The method of claim 1, wherein the anti-GM-CSF antibody is a nanobody or a camelid antibody.

7. The method of claim 1, wherein the anti-GM-CSF antibody is an antibody fragment that is a Fab, a Fab', a F(ab')$_2$, a scFv, or a dAB.

8. The method of claim 7, wherein the antibody fragment is conjugated to polyethylene glycol.

9. The method of claim 1, wherein the anti-GM-CSF antibody has an affinity of about 100 pM to about 10 nM.

10. The method of claim 1, wherein the anti-GM-CSF antibody has an affinity of about 0.5 pM to about 100 pM.

11. The method of claim 1, wherein the anti-GM-CSF antibody is a neutralizing antibody.

12. The method of claim 1, wherein the anti-GM-CSF antibody is a recombinant or chimeric antibody.

13. The method of claim 1, wherein the anti-GM-CSF antibody comprises a human variable region.

14. The method of claim 13, wherein the anti-GM-CSF antibody comprises a human light chain constant region.

15. The method of claim 13, wherein the anti-GM-CSF antibody comprises a human heavy chain constant region.

16. The method of claim 15, wherein the human heavy chain constant region is a gamma chain.

17. The method of claim 1, wherein the anti-GM-CSF antibody binds to the same epitope as chimeric 19/2.

18. The method of claim 17, wherein the anti-GM-CSF antibody comprises the $V_H$ and $V_L$ regions of chimeric 19/2.

19. The method of claim 18, wherein the anti-GM-CSF antibody comprises a human heavy chain constant region.

20. The method of claim 19, wherein the human heavy chain constant region is a gamma region.

21. The method of claim 17, wherein the anti-GM-CSF antibody comprises the $V_H$ region and $V_L$ region CDR1, CDR2, and CDR3 of chimeric 19/2.

22. The method of claim 1, wherein the anti-GM-CSF antibody is a human antibody.

23. The method of claim 1, wherein the anti-GM-CSF antibody has a half-life of about 7 to about 25 days.

24. The method of claim 1, wherein the anti-GM-CSF antibody is administered at a dose between about 1 mg/kg of body weight and about 10 mg/kg of body weight.

25. The method of claim 1, wherein the anti-GM-CSF antibody is administered intravenously.

26. The method of claim 1, wherein the anti-GM-CSF antibody is administered subcutaneously.

27. The method of claim 1, wherein the anti-GM-CSF antibody is administered intramuscularly.

28. The method of claim 1, wherein the anti-GM-CSF antibody is administered multiple times.

* * * * *